(12) United States Patent
Ikeda

(10) Patent No.: US 8,186,322 B2
(45) Date of Patent: May 29, 2012

(54) IGNITION APPARATUS, INTERNAL-COMBUSTION ENGINE, IGNITION PLUG, PLASMA EQUIPMENT, EXHAUST GAS DEGRADATION APPARATUS, OZONE GENERATING/STERILIZING/DISINFECTING APPARATUS, AND ODOR ELIMINATING APPARATUS

(75) Inventor: Yuji Ikeda, Kobe (JP)

(73) Assignee: Imagineering, Inc. (JP)

( * ) Notice: Subject to any disclaimer, the term of this patent is extended or adjusted under 35 U.S.C. 154(b) by 0 days.

(21) Appl. No.: 13/242,054

(22) Filed: Sep. 23, 2011

(65) Prior Publication Data

US 2012/0012077 A1    Jan. 19, 2012

Related U.S. Application Data

(62) Division of application No. 12/083,608, filed as application No. PCT/JP2006/319850 on Oct. 4, 2006.

(30) Foreign Application Priority Data

Sep. 20, 2006    (JP) .................................. 2006-255109

(51) Int. Cl.
*F02P 23/00* (2006.01)
(52) U.S. Cl. ..................... 123/143 B; 123/536
(58) Field of Classification Search .................. 123/536, 123/143
See application file for complete search history.

(56) References Cited

U.S. PATENT DOCUMENTS

| | | | |
|---|---|---|---|
| 4,297,983 A * | 11/1981 | Ward | 123/193.6 |
| 4,403,504 A | 9/1983 | Krage et al. | |
| 4,437,338 A | 3/1984 | Wilson | |
| 5,845,480 A | 12/1998 | DeFreitas et al. | |
| 6,581,581 B1 | 6/2003 | Bebich | |
| 7,671,309 B2 | 3/2010 | Kumar et al. | |
| 7,770,551 B2 | 8/2010 | Gallatz et al. | |
| 7,793,632 B2 | 9/2010 | Idogawa et al. | |
| 2002/0053336 A1 | 5/2002 | Nogi et al. | |
| 2007/0240660 A1 | 10/2007 | Gallatz et al. | |
| 2009/0266325 A1 | 10/2009 | Kumar et al. | |

FOREIGN PATENT DOCUMENTS

| | | |
|---|---|---|
| JP | 57-119164 | 7/1982 |
| JP | 57-186067 | 11/1982 |
| JP | 03-031579 | 2/1991 |
| JP | 2000-230426 | 8/2000 |
| JP | 2000-274249 | 10/2000 |
| JP | 2001-003800 | 1/2001 |
| JP | 2001-035692 | 2/2001 |
| JP | 2001-073920 | 3/2001 |
| JP | 2004-087498 | 3/2004 |
| JP | 2004-172044 | 6/2004 |

* cited by examiner

*Primary Examiner* — Stephen K Cronin
*Assistant Examiner* — Arnold Castro
(74) *Attorney, Agent, or Firm* — Bacon & Thomas, PLLC

(57) ABSTRACT

Stable and highly efficient combustion/reaction is provided, even when fuel ratio of mixture is decreased and combustion/reaction of the lean mixture is performed in a heat engine such as a reciprocating engine, for controlling dielectric constant of mixture in a combustion/reaction chamber 8 by introducing water and/or exhaust gas into the combustion/reaction chamber, by introducing water and/or exhaust gas into the combustion/reaction chamber. A microwave radiation antenna for irradiation of the combustion/reaction chamber, and a discharge unit for igniting the mixture in the combustion/reaction chamber are provided. The dielectric constant of the mixture before the combustion/reaction of the mixture is controlled so that the resonance frequency of the mixture corresponds to the frequency of the microwave.

4 Claims, 12 Drawing Sheets

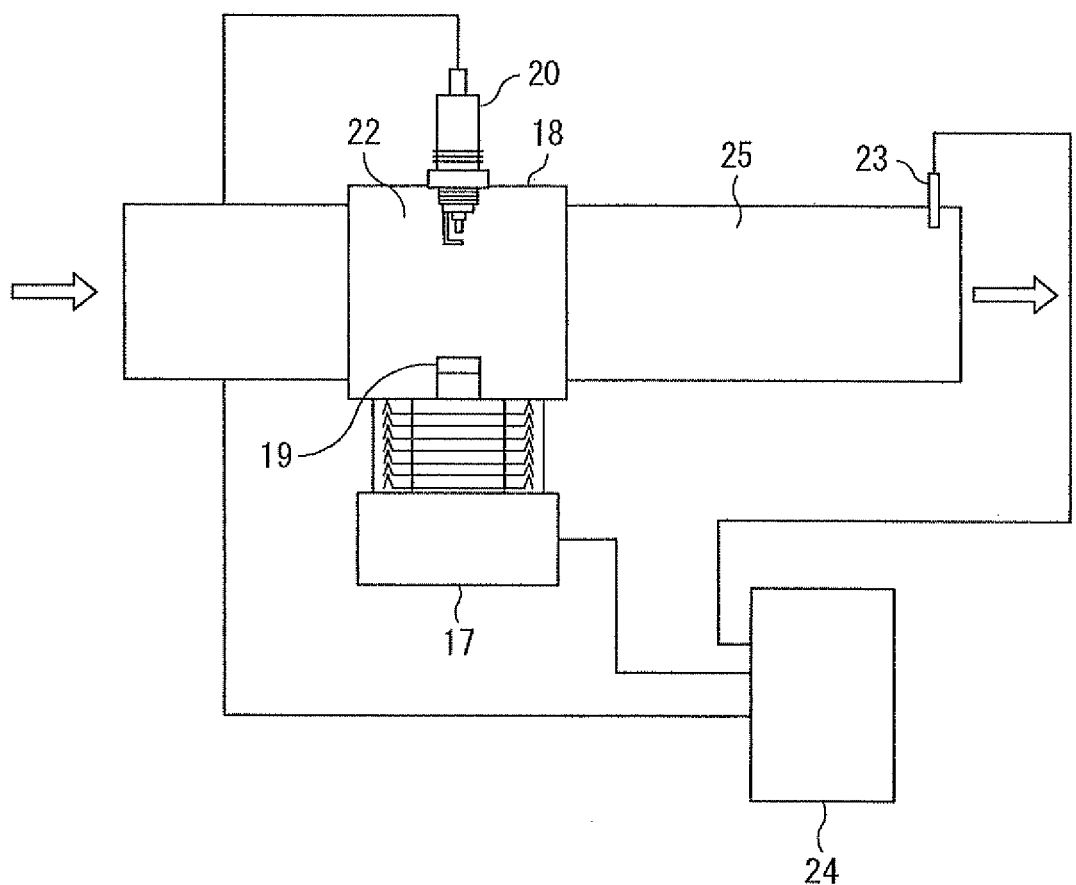
F I G . 12

IGNITION APPARATUS, INTERNAL-COMBUSTION ENGINE, IGNITION PLUG, PLASMA EQUIPMENT, EXHAUST GAS DEGRADATION APPARATUS, OZONE GENERATING/STERILIZING/DISINFECTING APPARATUS, AND ODOR ELIMINATING APPARATUS

CROSS-REFERENCE TO RELATED APPLICATIONS

This application is a Divisional Application of Ser. No. 12/083,608, filed on Apr. 15, 2008 which is a National Phase Application (35 USC 371) of PCT/JP2006/319850, filed on Oct. 4, 2006 and claims priority under 35 USC 119 of Japanese Application No. 2006-255109, filed Sep. 20, 2006.

The teachings of Japanese Application No. 2006-255109, filed Sep. 20, 2006 are incorporated herein in their entirety, inclusive of the specification, claims and drawings.

FIELD OF ART

The present invention relates to an ignition apparatus used in a heat engine such as a reciprocating engine, a rotary engine, a jet engine and a gas turbine, or a plasma equipment.

The present invention relates to an internal-combustion engine to which the ignition apparatus according to the present invention is suitably applied.

The present invention relates to an ignition plug that is suitably applied to the ignition apparatus according to the present invention.

The present invention relates to a plasma equipment that is used in an environmental (an in-plant and an end-of-pipe) countermeasure field such as decrease and reduction in hazardous effluents ($CO_2$, $NO_x$, and unburned hydrocarbon), volatile organic compounds (VOC), suspended particulate matters (PM), soot and the like or process and reuse of tar, sludge and drainage, and a medical/hygiene field such as sterilization, pasteurization and cleaning technologies.

The present invention relates to an exhaust gas degradation apparatus to which the plasma equipment according to the present invention is suitably applied.

The present invention relates to an ozone generating/sterilizing/disinfecting apparatus and an odor eliminating apparatus to which the plasma equipment according to the present invention is suitably applied.

BACKGROUND ART

In the past, ignition of mixture in an internal-combustion engine such as a reciprocating engine and a rotary engine was carried out by an ignition plug for performing spark discharge. However, there has been suggested an ignition apparatus that performs ignition using electromagnetic wave with frequency of several gigahertzes (GHz), that is microwave irrespective of the spark discharge, since electromagnetic noise that occurs by the spark discharge causes erroneous operation of an electronic device mounted on a vehicle.

For example, the ignition apparatuses in which a microwaveguide is configured to be connected to a combustion/reaction chamber (in a cylinder) and a discharge electrode for making microwave discharge is provided in the combustion/reaction chamber is disclosed in Patent Documents 1 to 4.

In the ignition apparatus, microwave pulses generated by a microwave generation unit (magnetron) are transmitted through the microwaveguide to the inside of the combustion/reaction chamber and microwave corona discharge is caused by the discharge electrode to ignite mixture in the combustion/reaction chamber.

For example, according to Patent Document 5, there is disclosed a gasoline internal-combustion engine in which a high frequency electric field generator (magnetron) is provided in the combustion/reaction chamber (in a cylinder) so that the high frequency electric field generator forms a high frequency electric field in the combustion chamber during the step of a compression stroke of the engine to perform dielectric heat, ignite, and burn mixture in the combustion chamber.

In the conventional plasma equipments used in the environmental countermeasure technologies, in general, high-temperature thermal equilibrium plasma is generated by increasing energy input into plasma generated by making discharge under low pressure to heat hazardous effluents, chemical substances, suspended particulate matters, soot and the like to high temperature so as to oxidize and degrade them.

Recently, a method (coaxial resonator-type plasma generation) of generating atmospheric thermal non-equilibrium plasma by microwave discharge has been studied. The generated plasma is reactive plasma in which temperature of electron is tens of thousands and temperature of gas is in the range of normal temperature to 1,000° C. In addition, a plasma equipment for a sterilization/disinfecting/odor elimination used in a medical/hygiene field has been developed by using effect of strong chemical reaction of OH radical, $O_3$ (ozone), and the like generated by the plasma (Innovation Japan 2005; http://ccr.ccr.tokushima-u.ac.jp/topic/050927-01.pdf).

A plasma equipment using the microwave allows gas with the pressure close to the atmospheric pressure to be excited by the microwave so as to generate plasma gas.

For example, a microwave plasma equipment is disclosed in Patent Documents 6 and 7. In the microwave plasma equipment, a non-metal pipe for a gas flow channel is disposed along the center of a central conductor, and gases injected from one end are excited by the microwave at a gap where the non-metal pipe is not covered with the central conductor, and then are induced plasma (coaxial resonator-type plasma generation) and discharged from the other end.

[Patent Document 1] JP-A-57-186067
[Patent Document 2] JP-A-3-31579
[Patent Document 3] JP-A-2000-230426
[Patent Document 4] JP-A-2001-73920
[Patent Document 5] JP-A-2000-274249
[Patent Document 6] JP-A-2001-035692
[Patent Document 7] JP-A-2004-172044

DISCLOSURE OF THE INVENTION

However, in recent years, it is required to improve fuel consumption rate in a heat engine such as a reciprocating engine, a rotary engine, a jet engine and a gas turbine, or a plasma equipment. In order to improve the fuel consumption rate, it may be supposed that fuel ratio of mixture is decreased and combustion/reaction of the lean mixture is performed. However, when the fuel ratio of the mixture of a conventional internal-combustion engine and the like is decreased, stability of combustion/reaction is impaired, for example, its cycle fluctuates. As a result, problems such as output degradation occur.

Accordingly, in order to improve the fuel consumption rate in the heat engine or the plasma equipment, it is necessary to perform the stable and highly efficient combustion/reaction even when the fuel ratio of the mixture is decreased and the combustion/reaction of the lean mixture is performed.

The ignition apparatus using the above-mentioned microwave corona discharge can be hardly put to practical use, since fuel consumption rate improvement and stability of the combustion/reaction cannot be expected comparing with an ignition method using the conventional spark discharge.

In addition, in the gasoline internal-combustion engine using the above-mentioned high frequency electric field generator, the magnetron is directly mounted on the engine, so that there is occurrence of various troubles in terms of durability, vibration resistance, limitations of mounting space, ambient temperature (that is, temperature of an engine increases), and malfunction prevention of a control system due to microwave leakage. For this reason, the gasoline internal-combustion engine of this kind can be hardly put to practical use.

The present invention is therefore contrived in view of the above-mentioned problems, and its object is to provide an ignition apparatus capable of achieving improvement of output, exhaust gas cleaning, and improvement of fuel consumption rate by performing the stable and highly efficient combustion/reaction even when the fuel ratio of the mixture is decreased and the combustion/reaction of the lean mixture is performed in a heat engine such as a reciprocating engine, a rotary engine, a jet engine and a gas turbine, or a plasma equipment.

In addition, an object of the present invention is to provide an internal-combustion engine capable of solving the various troubles in terms of durability, vibration resistance, limitations of mounting space, and ambient temperature (that is, temperature of an engine increases), and malfunction of a control system due to microwave leakage caused when a magnetron is directly mounted on an engine in the gasoline internal-combustion engine.

An object of the present invention is to provide the internal-combustion engine to which the ignition apparatus mentioned above according to the invention is suitably applied. In addition, an object of the present invention is to provide an ignition plug suitably applied to the ignition apparatus mentioned above according to the present invention.

In addition, in a conventional plasma generation method, a great amount of energy is spent in order to continuously generate a high-temperature plasma, the apparatus itself is very expensive (3,000,000 yen or more), running cost is relatively expensive, and transportation is difficult since the apparatus itself is large in size. Further, research and development of a technology using the atmospheric thermal nonequilibrium plasma have been just started. The above-mentioned discharge between the central conductors is used for plasma ignition, but large output (in the range of several hundreds of W to 5 kW or so) is still necessary so as to continuously generate stable plasma. At present, in the field of an environmental countermeasure technology and an application technology for a medical/hygiene field using the plasma equipment, low price is demanded for product performance of such countermeasure technology. For example, price is 300,000 yen or less per unit and electricity expense is around 30,000 yen per month for a small-size VOC process apparatus processing less than 1 ton per year (Ministry of Economy, 2004; chemical material risk reduction technology objective).

The plasma according to the present invention is microwave plasma of low-temperature/atmospheric pressure air. In the plasma, hazardous effluents, chemical substances, suspended particulate matter, soot, and the like are not heated in high temperature, but are oxidized and reacted chemically by products generated by the plasma (OH radical and ozone ($O_3$)), so that the hazardous effluents and the like is decreased, reduced, and detoxified. The plasma has a totally different novelty and effectiveness from the conventional technology using the high temperature plasma. In the past, much energy and a large-sized apparatus are required to generate the plasma for detoxifying the hazardous effluents. In addition, there has been few low-priced and small-sized apparatus capable of easily inducing plasma in atmospheric pressure air and generating a great amount of radicals.

For this reason, the present invention is contrived in view of the above-mentioned circumstance, and its object is to provide a low-priced and small-sized plasma equipment capable of easily inducing plasma in atmospheric pressure air and generating a great amount of radicals.

Another object of the present invention is to provide the plasma equipment capable of being applied to not only the end-of-pipe countermeasure technology but the in-plant countermeasure technology. Further, an object of the present invention is to provide the suitable plasma equipment capable of performing stable and highly efficient combustion in various combustors so that combustion process is improved (energy saving by volumetric ignition and extension of the combustion limit of lean fuel owing to chemical oxidization and reaction by strong OH radicals) and the hazardous effluents are decreased and reduced by decomposing and completely burning of unburned fuel without reducing output of power.

Still another object of the present invention is to provide an effective exhaust gas degradation apparatus, an ozone generating/sterilizing/disinfecting apparatus, and an odor eliminating apparatus by generating a great amount of OH radicals and $O_3$ that is continuously active at low cost.

In order to solve the above-mentioned problems and achieve the above-mentioned object, an ignition apparatus according to the present invention includes any one of the following configurations.

[Configuration 1]

According to an aspect of the invention, there is provided an ignition apparatus including dielectric constant control means for controlling dielectric constant of mixture in a combustion/reaction field by introducing water and/or exhaust gas generated from the combustion/reaction field into the combustion/reaction field where combustion/reaction or plasma reaction of the mixture is carried out, the mixture of reactive gas and oxidation gas existing in a heat engine or a plasma equipment; microwave radiation means for radiating microwave into the combustion/reaction field so as to increase temperature of the mixture in the combustion/reaction field and performing plasma discharge in the combustion/reaction field so as to increase radical concentration, so that characteristics of flame ignition is improved and flame propagation speed is promoted; ignition means for igniting the mixture in the combustion/reaction field by making discharge; and microwave radiation means for making discharge in the mixture in the combustion/reaction field so as to increase radical concentration in combustion/reaction or plasma gas, so that the characteristics of the flame ignition is improved and the flame propagation speed is promoted, wherein the dielectric constant control means controls the dielectric constant of the mixture before the combustion/reaction of the mixture is carried out in the combustion/reaction field so as to allow resonance frequency of the mixture in the combustion/reaction field to resonate with frequency of the microwave radiated from the microwave radiation means.

[Configuration 2]

According to another aspect of the invention, there is provided an ignition apparatus including dielectric constant control means for controlling dielectric constant of mixture in a combustion/reaction field by introducing water and/or exhaust gas generated from the combustion/reaction field into the combustion/reaction field where combustion/reaction or plasma reaction of the mixture is carried out, the mixture of reactive gas and oxidation gas existing in a heat engine or a plasma equipment; microwave radiation means for radiating microwave into the combustion/reaction field so as to increase temperature of the mixture in the combustion/reaction field and performing plasma discharge in the combustion/reaction field so as to increase radical concentration, so that characteristics of flame ignition is improved and flame propagation speed is promoted; ignition means for igniting the mixture in the combustion/reaction field by making discharge; microwave radiation means for performing plasma discharge in the combustion/reaction field so as to increase radical concentration in the combustion/reaction field, so that the characteristics of the flame ignition is improved and the flame propagation speed is promoted; and control means for controlling the microwave radiation means and the ignition means, wherein the microwave radiation means and the ignition means are controlled by the control means so as to repeat a cycle that is a process by which the microwave radiation means radiates the microwave into the combustion/reaction field to increase the temperature of the mixture in the combustion/reaction field and makes the plasma discharge in the combustion/reaction field to increase the radical concentration, so that the characteristics of the flame ignition is improved and the flame propagation speed is promoted; the ignition means ignites the mixture using the discharge; and then the microwave radiation means makes the plasma discharge in the combustion/reaction field by radiating the microwave into the combustion/reaction field to increase the radical concentration, so that the characteristics of the flame ignition is improved, the flame propagation speed is promoted, and the combustion/reaction of the mixture is promoted in the combustion/reaction field.

[Configuration 3]

In the ignition apparatus according to Configuration 1 or 2, a microwave radiation antenna serving as the microwave radiation means and an ignition/discharge unit serving as the ignition means may be further provided, wherein the microwave radiation antenna and the ignition/discharge unit are provided in an integrally formed insulator.

[Configuration 4]

In the ignition apparatus according to any one of Configurations 1 to 3, the microwave radiated from the microwave radiation means may be one or more controlled intermittent wave.

An internal-combustion engine according to the present invention includes any one of the following configurations.

[Configuration 5]

According to an aspect of the invention, there is provided an internal-combustion engine including a combustion/reaction chamber including a cylinder and a piston where mixture of reactive gas and oxidation gas is provided and combustion/reaction or plasma reaction of the mixture are carried out; and microwave radiation means for radiating microwave into the combustion/reaction chamber so as to increase temperature of the mixture in the combustion/reaction chamber and for making plasma discharge in the combustion/reaction chamber so as to increase radical concentration, so that characteristics of flame ignition is improved and flame propagation speed is promoted, wherein a concave unit for preventing leakage of the microwave is formed on an outer peripheral surface of the piston coming in contact with an inner wall of the cylinder.

[Configuration 6]

According to another aspect of the invention, there is provided an internal-combustion engine including a combustion/reaction chamber including a cylinder and a piston where mixture of reactive gas and oxidation gas is provided and combustion/reaction or plasma reaction of the mixture are carried out; a valve for opening and closing an inlet port and an outlet port provided on the combustion/reaction chamber; and microwave radiation means for radiating microwave into the combustion/reaction chamber so as to increase temperature of the mixture in the combustion/reaction chamber and for making plasma discharge in the combustion/reaction chamber so as to increase radical concentration, so that characteristics of flame ignition is improved and flame propagation speed is promoted, wherein an architecture for focusing the microwave on one or more bottom surfaces of the valve is formed on a surface of the valve facing the combustion/reaction chamber.

[Configuration 7]

According to still another aspect of the invention, there is provided an internal-combustion engine including a combustion/reaction chamber including a cylinder and a piston where mixture of reactive gas and oxidation gas is provided and combustion/reaction or plasma reaction of the mixture are carried out; ignition means for igniting the mixture in the combustion/reaction chamber by making discharge; and a magnet installed on a circumference of the ignition means or that of the cylinder, wherein a magnetic field generated from the magnet allows an electric field of ion or plasma generated in the combustion/reaction chamber to have a direction of the piston so that the ion or the plasma of burned/reacted gas in a flame/reaction zone or in a post stage of the flame/reaction zone is accelerated to an outer peripheral side of the cylinder.

In the internal-combustion engine, characteristics of the ignition by using the plasma generated by the microwave in flame surface and its post stage and acceleration of the flame propagation speed are promoted.

[Configuration 8]

According to still another aspect of the invention, there is provided an internal-combustion engine including a combustion/reaction chamber including a cylinder and a piston where mixture of reactive gas and oxidation gas is provided and combustion/reaction or plasma reaction of the mixture are carried out; ignition means for igniting the mixture in the combustion/reaction chamber by making discharge; and voltage regulation means for regulating voltage supplied to the ignition means, wherein the voltage regulation means controlling voltage supplied to the ignition means makes discharge below the ignition energy for unburned/unreacted mixture in the combustion/reaction chamber to induce plasma in the mixture and/or discharge for burned/reacted mixture to induce plasma in the mixture.

In the internal-combustion engine, it is possible to generate the plasma in both before and after the ignition by applying the conventional spark plug without using the microwave. That is, in the internal-combustion engine, when voltage supplied to the ignition means is the intermittent wave and its amplitude and time length are controlled, it is possible to achieve generation of stable flame and acceleration of the flame propagation speed under a variety of conditions of load, mixture concentration, revolution speed, ignition timing and the like.

[Configuration 9]

According to still another aspect of the invention, there is provided an internal-combustion engine including a combustion/reaction chamber including a cylinder and a piston where mixture of reactive gas and oxidation gas is provided and combustion/reaction or plasma reaction of the mixture are carried out; autoignition means for automatically igniting the mixture by injecting the mixture of the reactive gas and the oxidation gas under high pressure to compress the mixture of the reactive gas and the oxidation gas and increase temperature; microwave radiation means for radiating the microwave into the combustion/reaction chamber; and control means for controlling the autoignition means and the microwave radiation means, wherein the microwave radiation means and the ignition means are controlled by the control means so as to repeat a cycle that is a process by which the microwave radiation means radiates the microwave into the combustion/reaction chamber so that a great amount of hydroxyl (OH) radical and ozone ($O_3$) are generated from moisture of the mixture in the combustion/reaction chamber and then oxidizes and reacts chemically; and the autoignition means ignites the mixture, so that the combustion of the mixture in the combustion/reaction chamber is promoted by the great amount of hydroxyl (OH) radical and ozone ($O_3$).

[Configuration 10]

In the internal-combustion engine according to Configuration 5 or 9, measurement sensors for measuring densities of $O_2$, $NO_x$, CO, and soot of gas exhausted from the combustion/reaction chamber may be further provided, to the combustion/reaction or the plasma reaction of the mixture of the reactive gas and the oxidation gas is carried out in the combustion/reaction chamber. As a result, it is possible to carry out a combustion control in a manner that the combustion state is measured in real time so as to reduce the exhaust gas.

An ignition plug according to the present invention includes the following configuration.

[Configuration 11]

According to an aspect of the invention, there is provided an ignition plug including a microwave radiation antenna for radiating microwave into a combustion/reaction field where combustion/reaction of mixture is carried out, the mixture of reactive gas and oxidation gas existing in a heat engine or a plasma equipment; and an ignition/discharge unit for igniting the mixture in the combustion/reaction field, wherein the microwave radiation antenna and the ignition/discharge unit are provided in an integrally formed insulator.

A plasma equipment according to the present invention includes the following configuration.

[Configuration 12]

According to an aspect of the invention, there is provided a plasma equipment including a microwave oscillator for generating a predetermined microwave band; a microwave resonant cavity for allowing the predetermined microwave band to resonate; and microwave radiation means for radiating the microwave into the microwave resonant cavity, wherein the microwave radiation means is a microwave radiation antenna having the shape and the size so as to form a strong electric field of the microwave in a plasma generation field formed by the microwave.

[Configuration 13]

In the plasma equipment according to Configuration 12, plasma ignition means that makes partial discharge in gas in the microwave resonant cavity and then induces plasma in the gas may be further provided.

[Configuration 14]

In the plasma equipment according to Configuration 13, control means for controlling the microwave radiation means and the plasma ignition means and a measurement unit for measuring the generation amount or emission intensity of OH radicals and $O_3$ generated by plasma generation may be further provided, wherein the microwave radiation means and/or the plasma ignition means process the result of the measurement unit in real time so as to provide the resultant to the control means.

[Configuration 15]

In the plasma equipment according to Configuration 13 or 14, the microwave radiation means may include an ignition/discharge unit serving as the microwave radiation means and the plasma ignition means, and the microwave radiation means and the ignition/discharge unit may be provided in an integrally formed insulator.

[Configuration 16]

In the plasma equipment according to any one of Configurations 12 to 15, a magnetron for home electric appliances having an oscillation frequency of 2.45 GHz may be used as the microwave oscillator.

[Configuration 17]

In the plasma equipment according to any one of Configurations 13 to 15, the plasma ignition means may use barrier discharge which inserts an insulating material such as a dielectric body between electrodes, corona discharge which forms a non-uniform electric field, and pulse discharge which applies less than 1 μs of short pulse voltage.

[Configuration 18]

In the plasma equipment according to Configurations 12, 13, 15, or 16, microwave transmission means may be further provided.

[Configuration 19]

In the plasma equipment according to Configuration 18, the microwave transmission means may be a coaxial cable.

[Configuration 20]

In the plasma equipment according to Configuration 18, the microwave transmission means may be a waveguide.

[Configuration 21]

In the plasma equipment according to any one of Configurations 15 to 17, a coaxial cable for transmitting the microwave; a directional coupler for branching, isolating, and coupling the microwave; and a regulator for regulating impedance of entire transmission systems may be further provided.

An exhaust gas degradation apparatus according to the present invention includes the following configuration.

[Configuration 22]

According to an aspect of the invention, there is provided an exhaust gas degradation apparatus including a microwave oscillator for generating a predetermined microwave band; a microwave resonant cavity for allowing the predetermined microwave band to resonate; and microwave radiation means for radiating the microwave into the microwave resonant cavity, wherein the microwave radiation means is a microwave radiation antenna that is disposed on an outer circumference of a flow passage for exhaust gas in circumferential direction of the exhaust gas and that has the shape and the size so as to allow a plasma generation field formed by the microwave to uniformly form a strong electric field of the microwave on a section of the flow passage.

[Configuration 23]

In the exhaust gas degradation apparatus according to Configuration 22, a hollow or solid-core metallic bar or plate for forming the strong electric field of the microwave along a central axis of the flow passage in which the exhaust gas flows may be further provided.

[Configuration 24]

In the exhaust gas degradation apparatus according to Configuration 22 or 23, plasma ignition means that makes partial discharge in gas in the microwave resonant cavity and then induces plasma in the gas may be further provided.

[Configuration 25]

In the exhaust gas degradation apparatus according to Configuration 24, the plasma ignition means may be carried out by arc discharge between electrodes disposed in a circumferential direction of the flow passage in which the exhaust gas flows and opposed to each other in an axis direction.

[Configuration 26]

In the exhaust gas degradation apparatus according to any one of Configurations 22 to 25, microwave transmission means may be further provided.

[Configuration 27]

In the exhaust gas degradation apparatus according to Configuration 26, the microwave transmission means may be a coaxial cable.

[Configuration 28]

In the exhaust gas degradation apparatus according to Configuration 26, the microwave transmission means may be a waveguide.

An ozone generating/sterilizing/disinfecting apparatus according to the present, invention includes the following configuration.

[Configuration 29]

According to an aspect of the present invention, there is provided an ozone generating/sterilizing/disinfecting apparatus including a microwave oscillator for generating a predetermined microwave band to an ozone generation field; a microwave resonant cavity disposed on the ozone generation field for allowing the predetermined microwave band to resonate; and microwave radiation means for radiating the microwave into the microwave resonant cavity, wherein the microwave radiation means is a microwave radiation antenna having the shape and the size so as to form a strong electric field of the microwave in the ozone generation field formed by the microwave.

[Configuration 30]

In the ozone generating/sterilizing/disinfecting apparatus according to Configuration 29, plasma ignition means that makes partial discharge in gas in the microwave resonant cavity and then induces plasma in the gas may be further provided, wherein the microwave radiation means is the microwave radiation antenna having the shape and the size so as to form the strong electric field of the microwave in the ozone generation field formed by the plasma ignition means.

[Configuration 31]

In the ozone generating/sterilizing/disinfecting apparatus according to Configuration 29 or 30, the gas in the microwave resonant cavity may be air which is at the atmospheric pressure or more.

[Configuration 32]

In the ozone generating/sterilizing/disinfecting apparatus according to Configuration 29 or 30, the gas in the microwave resonant cavity may be steam which is at the atmospheric pressure or more.

An odor eliminating apparatus according to the present invention includes the following configuration.

[Configuration 33]

According to an aspect of the invention, there is provided an odor eliminating apparatus including a microwave oscillator for generating a predetermined microwave band; a microwave resonant cavity for allowing the predetermined microwave band to resonate; and microwave radiation means for radiating the microwave into the microwave resonant cavity, wherein the microwave radiation means is a microwave radiation antenna having the shape and the size so as to form a strong electric field of the microwave in an odor elimination space in the microwave resonant cavity formed by the microwave.

[Configuration 34]

In the odor eliminating apparatus according to Configuration 33, a circulation unit and a circulation system for circulating odor elimination gas and liquid in the microwave resonant cavity may be further provided.

In an ignition apparatus having Configuration 1, dielectric constant control means controls dielectric constant of mixture in a combustion/reaction field so as to allow resonance frequency of the mixture in the combustion/reaction field to resonate with frequency of the microwave radiated from microwave radiation means. As a result, it is possible to efficiently increase temperature of the mixture when the microwave is radiated from the microwave radiation means.

In the ignition apparatus having Configuration 2, the microwave radiation means radiates the microwave into the combustion/reaction field to increase the temperature of the mixture in the combustion/reaction field, and then performs plasma discharge in the combustion/reaction field to increase radical concentration, so that characteristics of the flame ignition and flame propagation speed are promoted; ignition means ignites the mixture; and then the microwave radiation means radiates the microwave into the combustion/reaction field to promote the combustion/reaction of the mixture. As a result, it is possible to perform the stable and highly efficient combustion/reaction even when fuel ratio of mixture is decreased and combustion/reaction of the lean mixture or the non-uniform mixture is performed.

In the ignition apparatus having Configuration 3, a microwave radiation antenna serving as the microwave radiation means and an ignition/discharge unit serving as the ignition means are provided in an integrally formed insulator. As a result, a microwave radiation antenna and an ignition/discharge unit are compatible with a conventional spark plug.

In the ignition apparatus having Configuration 4, the microwave radiated from the microwave radiation means is one or more controlled intermittent wave. As a result, it is possible to perform discharge in multipoint. In addition, it is possible to momentarily generate plasma using the microwave without increasing power consumption.

In an internal-combustion engine having Configuration 5, a concave portion for preventing leakage of the microwave is formed on an outer peripheral surface of the piston coming in contact with an inner wall of the cylinder. As a result, it is possible to prevent the leakage of the microwave even when the above-mentioned ignition apparatus is used.

In an internal-combustion engine having Configuration 6, an architecture (an architecture having a ¼ length of wavelength used as an electric length) for focusing the microwave on one or more bottom surface of a valve is formed on a surface of the valve facing the combustion/reaction chamber. As a result, it is possible to perform an energy radiation such as discharge to the combustion/reaction field by resonance of the microwave supplied to the valve by using the above-mentioned ignition apparatus.

In an internal-combustion engine having Configuration 7, a magnetic field generated from the magnet allows an electric field of ion or plasma generated in the combustion/reaction chamber to have a direction of the piston so that the ion or the plasma of burned/reacted gas in a flame reaction zone or its post stage is accelerated to an outer peripheral side of the cylinder. As a result, it is possible to promote the characteristics of the flame ignition and acceleration of the flame propagation speed by using the plasma generated by the microwave in a flame surface and its post stage.

In an internal-combustion engine having Configuration 8, voltage regulation means controlling voltage supplied to the ignition means makes discharge below ignition energy for unburned/unreacted mixture in the combustion/reaction chamber to induce plasma in the mixture and/or discharge for burned/reacted mixture to induce plasma in the mixture. As a result, it is possible to generate the plasma in both before and after the ignition by applying the conventional spark plug without using the microwave.

That is, in the internal-combustion engine, when voltage supplied to the ignition means is the intermittent wave and its amplitude and its time length are controlled, it is possible to achieve generation of stable flame and acceleration of the flame propagation speed under a variety of conditions of load, mixture concentration, revolution speed, ignition timing and the like.

In an internal-combustion engine having Configuration 9, the microwave is radiated into the combustion/reaction field in advance when the mixture is automatically ignited by injecting the mixture of reactive gas and oxidization gas under high pressure to the combustion/reaction field to compress the mixture and increase temperature. As a result, it is possible to generate low-temperature plasma by using the autoignition. Then, a great amount of OH radical and ozone ($O_3$) can be continuously generated from moisture in the mixture by the generation of the low-temperature plasma. As a result, it is possible to promote combustion of the mixture in the combustion/reaction field.

In the internal-combustion engine having Configuration 10, measurement sensors for measuring densities of $O_2$, $NO_x$, CO, and soot of gas exhausted from the combustion/reaction chamber is provided, the combustion/reaction condition in the combustion/reaction chamber can be monitored. As a result, it is possible to reflect the resultant to a combustion improvement/control using the microwave.

In an ignition plug having Configuration 11, the microwave radiation antenna and the ignition/discharge unit are provided in an integrally formed insulator. As a result, it is possible to configure the above-mentioned ignition apparatus using the ignition plug compatible with plasma sources such as a conventional spark plug, a glow plug and the like.

In a plasma equipment having Configuration 12, a microwave oscillator for generating a predetermined microwave band; a microwave resonant cavity (cavity) for allowing the microwave of the predetermined band to resonate; and microwave radiation means (microwave radiation antenna) for radiating the microwave into the cavity are provided. As a result, it is possible to efficiently generate the low-temperature plasma by providing with a microwave radiation antenna having the shape and the size so as to form a strong electric field of the microwave in a plasma generation field.

In the plasma equipment having Configuration 13, plasma ignition means that makes partial discharge in gas in the cavity and then induces plasma in the gas is provided. As a result, it is possible to efficiently generate the low-temperature plasma by providing with a microwave radiation antenna having the shape and the size so as to form a strong electric field of the microwave in a plasma generation field.

In the plasma equipment having Configuration 14, control means for controlling the microwave radiation means and the plasma ignition means, and a measurement unit for measuring generation amount or emission intensity of OH radicals and $O_3$ generated by plasma generation are provided. As a result, it is possible to electrically control the generation amount of OH radicals and $O_3$ by processing result of the measurement unit in real time so as to provide the resultant for the control of the microwave radiation means and/or the plasma ignition means.

In the plasma equipment having Configuration 15, the microwave radiation antenna and the ignition/discharge unit are provided in the integrally formed insulator. As a result, it is possible to provide the plasma equipment that is low in cost and compact in size, easily handled and highly flexible.

In the plasma equipment having Configuration 16, a magnetron for home electric appliances in which an oscillation frequency is 2.45 GHz is used. As a result, it is possible to provide the plasma equipment that is low in cost, readily obtainable, easily repaired/exchanged, and free of legal regulations in use.

In the plasma equipment having Configuration 17, the plasma ignition means can obtain the same effect when any one of barrier discharge which inserts an insulating material such as a dielectric body between electrodes, corona discharge which forms a non-uniform electric field, or pulse discharge which applies less than 1 μs of short pulse voltage is used. As a result, it is possible to provide the plasma equipment that is flexible regardless of an application condition.

In the plasma equipment having Configuration 18, microwave transmission means is provided. As a result, it is possible to give installation flexibility of a generator while maintaining the same effect.

In the plasma equipment having Configuration 19, a flexible coaxial cable is used for the microwave transmission means. As a result, there are no limitations for installation of the microwave oscillator while maintaining the same effect, so it is possible to provide the flexible plasma equipment.

In the plasma equipment having Configuration 20, the microwave transmission means is a waveguide. As a result, it is possible to perform more efficient transmission than the coaxial cable.

In the plasma equipment having Configuration 21, a coaxial cable for transmitting the microwave; a directional coupler for branching, isolating, and coupling the microwave; and a regulator (stub) for regulating impedance of entire transmission systems are provided. As a result, it is possible to optimally perform the regulation in a state where the transmission efficiency of the microwave of the transmission systems is increased. In addition, the microwave oscillator and a plasma generation position can be separated from each other. As a result, it is possible to provide more margin for the system design according to application position.

In an exhaust gas degradation apparatus having Configuration 22, the microwave oscillator for generating a predetermined microwave band; the microwave resonant cavity (cavity) for allowing the microwave of the predetermined band to resonate; and the microwave radiation means (microwave radiation antenna) for radiating the microwave into the cavity are provided, and the microwave radiation means is disposed on the outer circumference of a flow passage for exhaust gas in the circumferential direction of the exhaust gas and has the shape and the size so as to allow a plasma generation field formed by the microwave to uniformly form a strong electric field of the microwave on a section of the flow passage. As a result, it is possible to process high-flow exhaust gas.

In the exhaust gas degradation apparatus having Configuration 23, a hollow or solid-core metallic bar or plate for forming a strong electric field of the microwave along a central axis of the flow passage (flow) in which the exhaust gas flows is provided. As a result, it is possible to generate the low-temperature plasma that is uniform and strong throughout a section of the flow passage in which the exhaust gas flows and along the flow direction.

In the exhaust gas degradation apparatus having Configuration 24, the plasma ignition means that makes partial discharge in gas in the cavity and then induce plasma in the gas is provided. As a result, it is possible to effectively perform degradation of the exhaust gas by energy-efficiently generating the plasma by the microwave in the cavity.

In the exhaust gas degradation apparatus having Configuration 25, the plasma ignition means is carried out by arc discharge between electrodes disposed in a circumferential direction of the flow passage in which the exhaust gas flows and opposed to each other in an axis direction (flow). As a result, it is possible to generate the plasma that is uniform in the section of the flow passage in an arbitrary section of the axis direction.

In the exhaust gas degradation apparatus having Configuration 26, the microwave transmission means is provided. As a result, it is possible to fix the plasma equipment on the online irrespective of the installation position of the microwave oscillator, eliminating installation limitation.

In the exhaust gas degradation apparatus having Configuration 27, the microwave transmission means is a coaxial cable. As a result, it is possible to fix the plasma equipment on the online irrespective of the installation position of the microwave oscillator, eliminating the need of a transmission space in a midstream and structural limitation for installation.

In the exhaust gas degradation apparatus having Configuration 28, the microwave transmission means is a waveguide. As a result, it is possible to perform a highly efficient transmission more than the coaxial cable.

In an ozone generating/sterilizing/disinfecting apparatus having Configuration 29, a microwave oscillator for generating a predetermined microwave band to an ozone generation field; a microwave resonant cavity (cavity) disposed on the ozone generation field for allowing the microwave of the predetermined band to resonate; and the microwave radiation means (microwave radiation antenna) for radiating the microwave into the cavity are provided, and the microwave radiation antenna has the shape and the size so as to form a strong electric field of the microwave in the ozone generation field. As a result, it is possible to generate high flow ozone.

In the ozone generating/sterilizing/disinfecting apparatus having configuration 30, the plasma ignition means that makes partial discharge in gas in the cavity and then induces plasma in the gas is provided, and the microwave radiation antenna has the shape and the size, which forms the strong electric field of the microwave in the ozone generation field formed by the plasma ignition means. As a result, it is possible to effectively generate high flow ozone by energy-efficiently generating the plasma by the microwave in the cavity.

In the ozone generating/sterilizing/disinfecting apparatus having Configuration 31, the gas in the cavity is air that is at the atmospheric pressure or more. As a result, it is possible to easily perform generation in a large amount at a low cost without any special structure.

In the ozone generating/sterilizing/disinfecting apparatus having Configuration 32, the gas in the cavity is steam which is at the atmospheric pressure or more is used. As a result, it is also possible to perform generation in a large amount at a low-cost and easy without any special structure.

In an odor eliminating apparatus having Configuration 33, a microwave oscillator for generating a predetermined microwave band; a microwave resonant cavity (cavity) for allowing the microwave of the predetermined band to resonate; and microwave radiation means (microwave radiation antenna) for radiating the microwave into the cavity are provided, and the microwave radiation antenna has the shape and the size so as to form a strong electric field of the microwave in an odor elimination space in the cavity formed by the microwave. As a result, it is possible to improve an odor elimination effect by generating a great amount of ozone.

In the odor eliminating apparatus having Configuration 34, a circulation unit and a circulation system for circulating an odor elimination gas and liquid are provided in the cavity. As a result, it is possible to provide the odor eliminating apparatus in which the odor elimination effect is further improved.

That is, the present invention provides an ignition apparatus capable of attaining stabilization of ignition, improvement of combustion speed, promotion of combustion of non-uniform mixture, and improvement of fuel consumption rate by performing the stable and highly efficient combustion/reaction even when fuel ratio of mixture is decreased and combustion/reaction of the lean mixture is performed in a heat engine such as a reciprocating engine, a rotary engine, a jet engine and a gas turbine, or a plasma equipment.

In addition, the present invention provides the internal-combustion engine to which the ignition apparatus according to the present invention is suitably applied. Further, the present invention provides the ignition plug suitably applied to the ignition apparatus according to the present invention. The ignition plug can be used as the ignition apparatus in the internal-combustion engine as well as a combustion/reaction device. Accordingly, it is possible to contribute to stabilization of the flame, improvement of fuel consumption, and improvement of combustion/reaction efficiency.

Furthermore, the present invention provides an inexpensive and compact apparatus that induces plasma easily at the atmospheric pressure and generates a great amount of OH radicals and $O_3$. The apparatus may be applied to a process device for decreasing and reducing hazardous effluents ($CO_2$, $NO_x$, and unburned hydrocarbon), volatile organic compound (VOC), suspended particulate matter (PM), soot, and the like. In addition, the apparatus may be applied to a plasma equipment, an exhaust gas degradation apparatus, a hazardous material process apparatus, an ozone generating/sterilizing/disinfecting apparatus, and an odor eliminating apparatus used in an environmental (an in-plant and an end-of-pipe) countermeasure field such as application to an electric dust collector and process and reuse of tar, sludge, and drainage, and a medical/hygiene field such as sterilization, pasteurization, and cleaning technologies.

In addition, the apparatus can be applied to not only the end-of-pipe countermeasure technology but the in-plant countermeasure technology. It is possible to provide the suitable plasma equipment capable of performing stable and highly efficient combustion in various combustors such as a gas turbine, a furnace, an incinerator, and a pyrolytic furnace so that a combustion process is improved (energy saving by extension of the combustion limit of lean fuel) and the hazardous effluents are decreased and reduced by decomposing and completely burning of unburned fuel without reducing output of power.

It is possible to provide the ozone generating/sterilizing/disinfecting apparatus and the odor eliminating apparatus easily generating a great amount of $O_3$ at a low cost, in a high-efficiently and energy saving manner.

BRIEF DESCRIPTION OF THE DRAWINGS

FIG. 12 is a side view showing a configuration of a main part of a plasma equipment according to a second embodiment of the present invention. In addition, FIG. 12 is a side view showing a configuration of a main part of an exhaust gas degradation apparatus according to a first embodiment of the present invention.

FIG. 14 is a side view showing a configuration of a main part of an exhaust gas degradation apparatus according to a second embodiment of the present invention.

DESCRIPTION OF REFERENCE NUMERALS AND SIGNS

Figure 1:
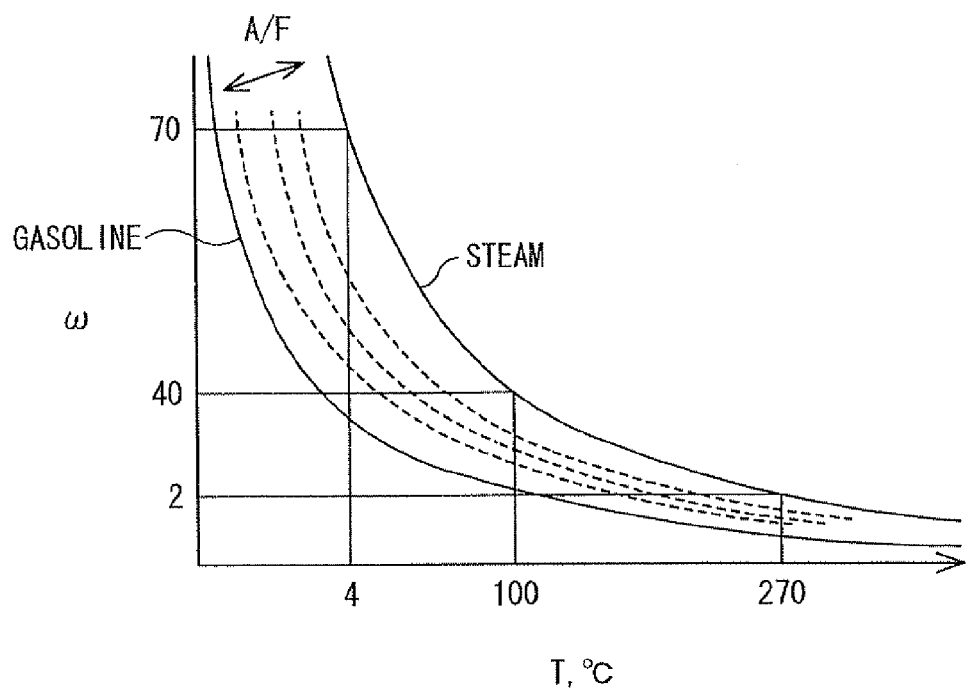
FIG. 1 is a graph showing correlation between temperature and dielectric constant of mixture in an internal-combustion engine to which an ignition apparatus according to the present invention is applied.

1: MICROWAVE RADIATION ANTENNA
2: IGNITION/DISCHARGE UNIT
3: COAXIAL CABLE
4: GROUND TERMINAL
5: ANODE TERMINAL
6: CYLINDER
7: PISTON
8: COMBUSTION/REACTION CHAMBER
9: CONCAVE PORTION
10: INLET PORT
11: OUTLET PORT
12: VALVE
13: PERIODIC ARCHITECTURE
14: SHAFT
15: MAGNET
16: INSULATING MATERIAL
17: MICROWAVE OSCILLATOR
18: MICROWAVE RESONANT CAVITY (CAVITY)
19: MICROWAVE RADIATION MEANS (MICROWAVE RADIATION ANTENNA)
20: PLASMA IGNITION MEANS
21: PLASMA GENERATION FIELD
22: FLUID IN CAVITY
23: MEASUREMENT UNIT
24: CONTROL MEANS
25: COAXIAL CABLE

[Best Mode for Carrying Out the Invention]

Hereinafter, embodiments of the invention will be described with reference to the drawings.

[First Embodiment of Ignition Apparatus]

In a heat engine or a plasma equipment, mixture of reactive gas and oxidation gas is provided. In a combustion/reaction field in which a combustion/reaction of the mixture is caused, for example, a combustion/reaction chamber of an engine, when temperature of the mixture is increased or ignition is carried out by microwave, it is necessary to efficiently transmit required energy to the combustion/reaction chamber for the purpose of the temperature increase or the ignition. For this reason, it is preferable that resonance frequency determined by the shape of the combustion/reaction chamber, dielectric constant ($\in$) of the mixture and the like corresponds to frequency of the microwave. On the other hand, as a magnetron used for generating the microwave, a number of the magnetrons which have a oscillating frequency of 2.45 GHz and allow water molecules to resonate are already manufactured and used for home electric appliances. In addition, as for a magnetron used for a fish detector and a radar, the magnetrons which have much higher frequency are commercially used.

If the resonance frequency of the combustion/reaction chamber can be corresponded with the frequency of 2.45 GHz for example, it is possible to use the magnetrons of 2.45 GHz distributed in large quantities and low in price. This is desirable as it permits easy and low-cost manufacturing of an apparatus.

However, since the shape of the combustion/reaction chamber depends on an inner shape of a cylinder and a shape of a piston that are determined by various factors other than the resonance frequency, it is difficult to make a shape that allows the resonance frequency fixed in all engines.

Thus, in an ignition apparatus according to the present invention, the dielectric constant ($\in$) of the mixture is controlled by introducing water and/or exhaust gas into the combustion/reaction chamber so that the resonance frequency of the mixture in the combustion/reaction chamber corresponds to the microwave frequency.

That is, the ignition apparatus includes a dielectric constant control means. The dielectric constant control means controls the dielectric constant of the mixture in a combustion/reaction field by introducing water and/or the exhaust gas which is exhausted from the combustion/reaction field into the combustion/reaction field (the combustion/reaction chamber or the like) in which combustion/reaction of the mixture of reactive gas and oxidation gas that exist in a heat engine or a plasma equipment is carried out.

Variation in the dielectric constant ($\in$) of the mixture in the combustion/reaction chamber depends on variation in air-fuel ratio (A/F value) by change of amount of gasoline which is injected into the combustion/reaction chamber. As shown in FIG. 1, the variation of the dielectric constant ($\in$) can also be caused by introducing water (steam) into the combustion/reaction chamber independent of the mixture. Thus, the dielectric constant of the mixture in the combustion/reaction chamber can be controlled by the dielectric constant control means by introducing water into the combustion/reaction chamber. A process of introducing water into the combustion/reaction chamber may be carried out in the manner that water stored in a tank is sent into the combustion/reaction chamber by a pump, for example.

In addition, a process of reintroducing the exhaust gas which is exhausted from the combustion/reaction chamber into the combustion/reaction chamber is called "EGR" (exhaust gas returning). Since the "EGR" is conventionally carried out, the known mechanism can be used as a specific mechanism for reintroducing the exhaust gas into the combustion/reaction chamber.

The dielectric constant control means controls an amount of steam or temperature in the combustion/reaction chamber by introducing water and/or the exhaust gas into the combustion/reaction chamber, so that the dielectric constant ($\in$) of the mixture is controlled. In addition, the dielectric constant control means controls the resonance frequency of the mixture in the combustion/reaction chamber to correspond to the microwave frequency that is radiated by a microwave radiation means described below.

The ignition apparatus includes the microwave radiation means for radiating the microwave into the combustion/reaction field so as to increase temperature of the mixture in the combustion/reaction field. A general magnetron which has an oscillation frequency of 2.45 GHz can be used as the microwave radiation means. The magnetron which has the oscillation frequency of 2.45 GHz is used in a so-called microwave oven and then manufactured and distributed in large quantities. On the other hand, the microwave radiation means is not limited to the magnetron, but a transmitter or the like of a high-frequency band used in a mobile phone or the like can also be used. In this case, it is possible to provide an apparatus that is smaller and portable. In addition, it is preferable that the microwave radiation means radiates the microwave as microsecond pulse or one or more of intermittent radiation. When the microwave is intermittently radiated, it is possible to generate plasma using the microwave having momentary high power without increasing power consumption.

Further, the oscillation form of the microwave can be controlled by configuring an optimal combination of pulse, intermittent radiation and continuous radiation for an object to which the present invention is applied.

Figure 2:
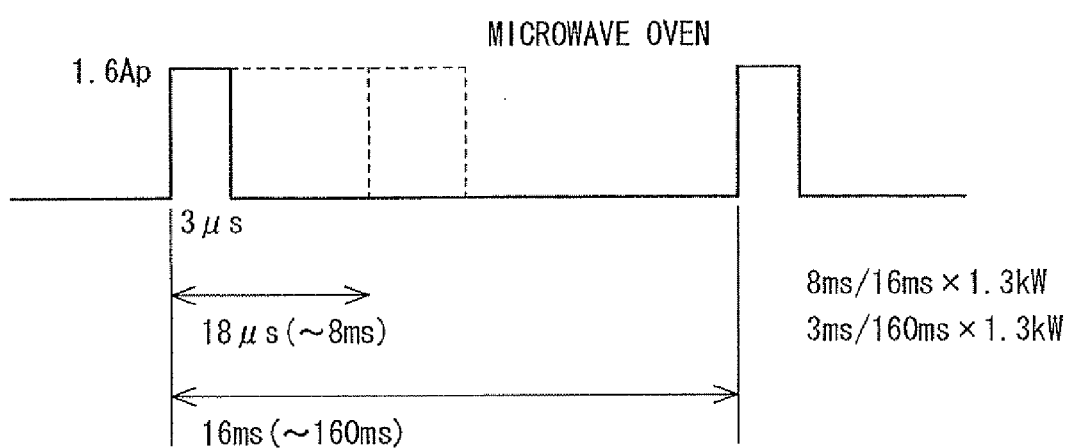
FIG. 2 is a graph showing pulse width of microwave in the ignition apparatus according to the present invention.

In addition, continuous duration (pulse width) of the intermittent microwave can be optimized by the heat engine or the plasma equipment respectively. For example, as shown in FIG. 2, when a mechanism of the microwave oven with an inverter is used, it is possible to radiate the microwave with a pulse width of 3 μsec to 18 μsec at the period of about 16 msec. Further, the amplitude and the period of intermittent microwave can be arbitrarily set.

In such an ignition apparatus, the microwave generated by the microwave radiation means is configured to be transmitted into the combustion/reaction chamber via a coaxial cable.

In addition, the ignition apparatus includes ignition means for igniting to the mixture in the combustion/reaction chamber. The ignition means that includes an ignition/discharge unit such as a spark plug that is generally used in a gasoline engine or a glow plug that is generally used in a diesel engine can be used.

In the ignition apparatus, as the ignition means, the microwave radiation means may be also used as the ignition means without using the spark plug or the glow plug. In addition, as the ignition means for easily generating a plasma by microwave, electrons may be thermally supplied thereto by means such as laser beam, flame of a lighter or a burner and the like, a heater and a metallic piece of high temperature.

In the ignition apparatus, the dielectric constant control means controls the dielectric constant ($\in$) of the mixture before the combustion/reaction of the mixture in the combustion/reaction chamber is carried out so that the resonance frequency of the mixture in the combustion/reaction chamber corresponds to the frequency of the microwave radiated by the microwave radiation means. In this state, when the microwave is radiated by the microwave radiation means, the entire combustion/reaction chamber resonates, and thus temperature of the mixture in the combustion/reaction chamber is efficiently increased so that the ignition easily occurs.

When the temperature of the mixture in the combustion/reaction chamber is increased, the ignition means carries out the ignition, and thus the combustion/reaction is satisfactorily caused in the mixture. In the ignition, so-called volumetric ignition, point ignition in a local region, or multistage ignition may be carried out by the use of resonance by the microwave. That is, the ignition apparatus is a system capable of generating plasma by using the microwave before the ignition, at the ignition time, and after the ignition.

In addition, ignition delay should be taken into consideration for the ignition timing. So it is preferable that the ignition is carried out at the predetermined time before the time when the piston reaches top dead center and the volume of the combustion/reaction chamber is thereby maximally compressed. Fuel concentration (air-fuel ratio) and ignition timing can be optimized by the heat engine or the plasma equipment respectively, thereby acquiring the maximum output of power.

In the ignition apparatus, the dielectric constant of the mixture can be accurately controlled by optimizing the amounts of water, recirculated exhaust gas, fuel, and the like introduced into the combustion/reaction chamber. Additionally, the optimization may be adequately determined in consideration of oxygen concentration, temperature of the mixture, residual gas concentration, and the like in the combustion/reaction chamber.

Accordingly, comparing with a conventional ignition apparatus used in a heat engine or a plasma equipment, the ignition apparatus can perform stable combustion/reaction even when fuel ratio in the mixture is low and mixture concentration is nonuniform.

Further, the ignition apparatus can be applied to a jet engine and the like that have no closed combustion/reaction chamber as a combustion/reaction field. In the jet engine and the like, intake, mixture, combustion/reaction and exhaust are sequentially carried out in continuous spaces of the engine. However, as described above, the ignition apparatus controls the dielectric constant of the mixture, radiates the microwave and performs ignition continuously or intermittently in the field in which the combustion/reaction operation is carried out.

Furthermore, in the ignition apparatus, the microwave radiation means is not limited to the magnetron having a oscillation frequency of 2.45 GHz, but may use a magnetron oscillating at resonance frequency of the hydrocarbon molecule, the carbon molecule, the hydrogen molecule, or the like in fuel. In this case, it is not necessary to introduce water into the combustion/reaction field.

[Second Embodiment of Ignition Apparatus]

The ignition apparatus according to the second embodiment includes the microwave radiation means and the ignition means in the same manner as the ignition apparatus according to the above-mentioned first embodiment. Further, the ignition apparatus includes control means for controlling the microwave radiation means and the ignition means.

Figure 3:
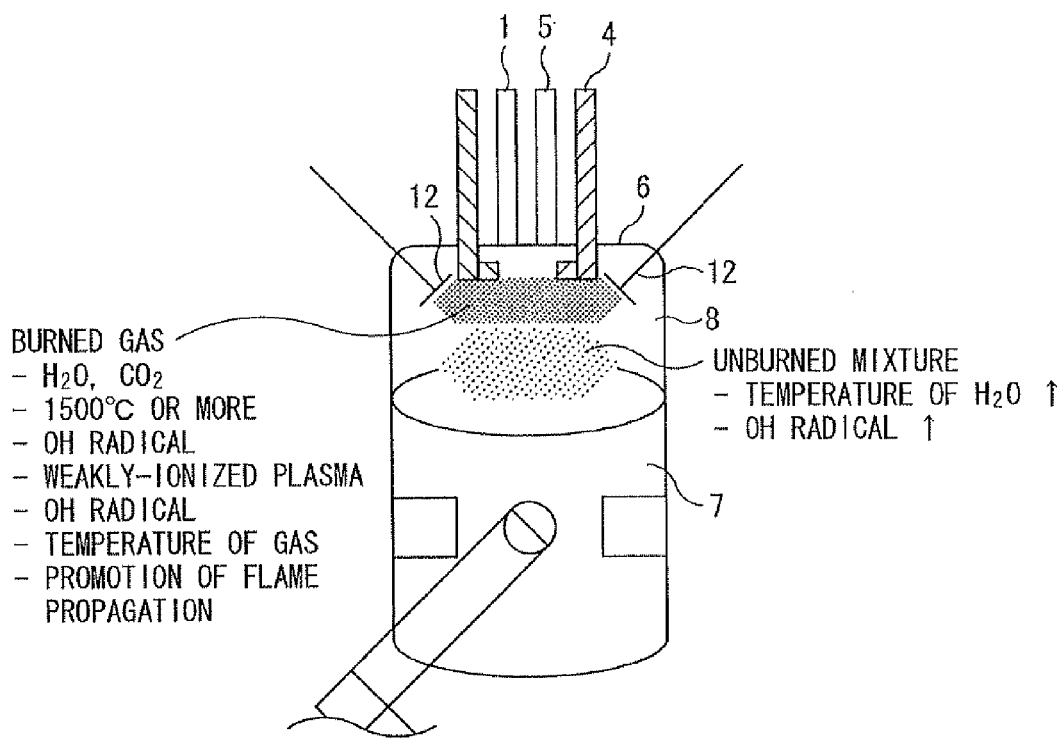
FIG. 3 is a side view showing a configuration of a combustion/reaction chamber in the internal-combustion engine.

The control means controls the microwave radiation means and the ignition means and performs following cycle repeatedly. The cycle comprises increasing the temperature of the mixture in the combustion/reaction chamber 8 or generating radicals by radiating the microwave into a combustion/reaction chamber 8 by the microwave radiation means as shown in FIG. 3, then performing the ignition to the mixture by the ignition means, next promoting the combustion/reaction of the mixture in the combustion/reaction chamber by radiating the microwave into the combustion/reaction chamber by the microwave radiation means.

That is, in this ignition apparatus, generation timing and output of power (input energy) of the microwave are controlled, thereby realizing a combustion/reaction cycle of temperature increase, radical generation, ignition and promotion of flame propagation in the mixture. At this time, water and/or exhaust gas may be introduced into the mixture before the combustion/reaction in the same manner as the above-mentioned first embodiment.

Further, in this ignition apparatus, for example, four-stage multipoint ignition can be carried out. In a fist stage, the microwave is radiated to the mixture before the ignition so as to increase the temperature of water in the mixture. In a second stage, the microwave is radiated to the mixture before the ignition so as to generate plasma discharge in the combustion/reaction field, thereby increasing radical concentration. In the first and second stages, the ignition characteristics of the mixture are enhanced, thereby enabling the ignition to easily occur. In a third stage, ignition is carried out by discharging in the mixture in the combustion/reaction field. At this time, the ignition may be carried out by using a conventional spark plug. In a fourth stage, the microwave is radiated to the mixture after the ignition so as to generate the plasma discharge in the combustion/reaction field, thereby increasing the radical concentration, or the microwave is radiated so as to generate a stationary wave by using the microwave, thereby promoting the flame propagation.

Figure 4:
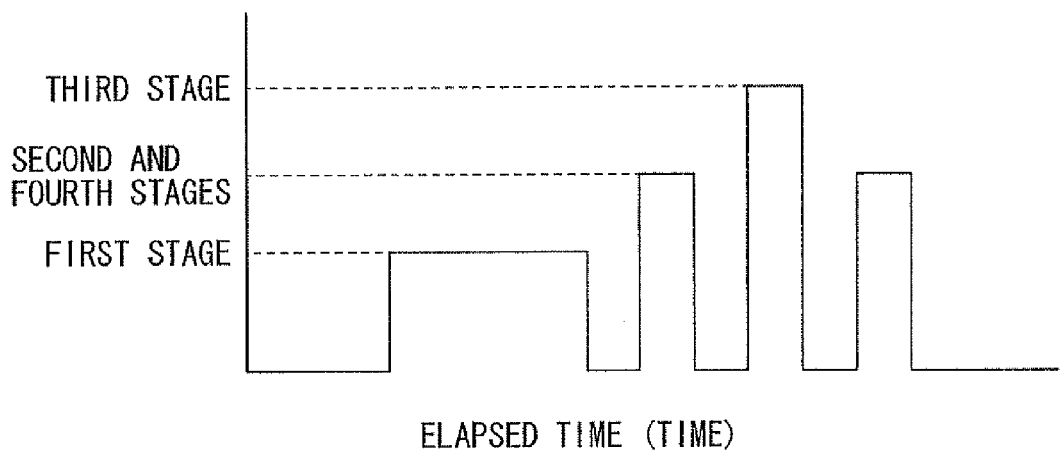
FIG. 4 is a graph showing pulse width and output of the microwave of a four-stage multipoint ignition according to the present invention.

In addition, as shown in FIG. 4, the pulse width and the output of power (input energy) of the microwave in the four-stage multipoint ignition can be configured to acquire the maximum output by optimizing the output and the pulse width of the microwave for each step in the heat engines or the plasma equipments. Further, temperature increase of the mixture, generation of radicals such as OH radicals, the ignition and the promotion of the flame propagation can be carried out by the microwave radiation by controlling the output of the microwave and amplitude and period of the intermittent wave.

In this ignition apparatus, the combustion/reaction operation is promoted as described above so that lean mixture that is not possible to perform combustion/reaction by a conventional ignition apparatus is now efficiently combusted/reacted, thereby improving fuel/reactant consumption rate, decreasing size of the combustion/reaction chamber, improving output, and cleaning the exhaust gas in a stable output state. Further, in this ignition apparatus, since imperfect combustion/reaction is prevented and complete combustion/reaction is realized, it is possible to suppress occurrences of air contaminants, thereby contributing to an environmental conservation.

[Embodiment of Ignition Plug]

Figure 5A:
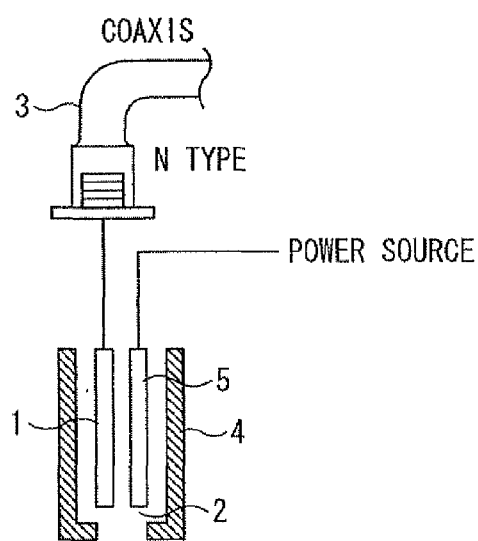
FIG. 5 are sectional views showing a configuration of an ignition plug according to the present invention.

As shown in FIG. 5A, an ignition plug according to the present invention includes a microwave radiation antenna 1 serving as the microwave radiation means and an ignition/discharge unit 2 serving as the ignition means. The microwave radiation antenna and the ignition/discharge unit are provided in an integrally formed insulator. The ignition plug is compatible with a spark plug and a glow plug generally used in the conventional gasoline engine and the conventional diesel engine, thereby constituting the above-mentioned ignition apparatus according to the present invention.

In this ignition plug, the microwave is transmitted from a magnetron (not shown) to the microwave radiation antenna 1 via a coaxial cable 3. Further, this ignition plug includes a cylindrical ground terminal 4 surrounding the microwave radiation antenna 1. The ignition/discharge unit 2 is formed between an end of an anode terminal 5 to which voltage is applied from a power source (not shown) and an end of the cylindrical ground terminal 4.

Figure 5B:
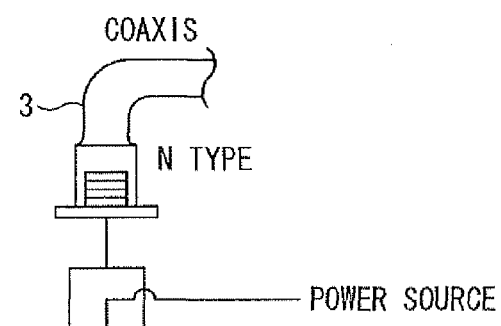

As shown in FIG. 5B, the ignition plug may be configured so that the microwave radiation antenna 1 is cylindrically shaped to house the anode terminal 5. In this case, the ground terminal 4 should be bar-shaped and disposed outside the microwave radiation antenna 1. In this case, the ignition/discharge unit 2 is formed between the ends of the anode terminal 5 and the ground terminal 4.

Figure 5B:
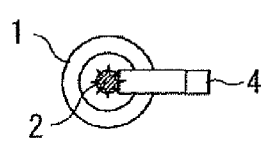
Figure 6:
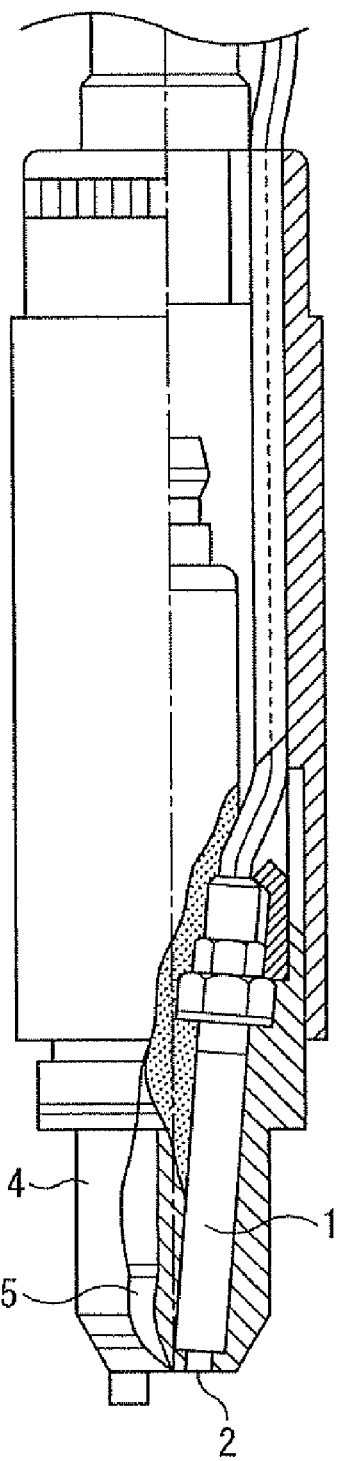
FIG. 6 is a side view showing the configuration of the ignition plug according to the present invention.

In the ignition plug, as shown in FIG. 6, the microwave radiation antenna 1 and the ignition/discharge unit 2 are integrally configured so as to be compatible with the conventional and general spark plug. Further, in the ignition plug, the spark (electrical discharge) serving as the ignition means and the microwave radiation serving as the microwave radiation means are possible, thereby easily configuring the above-mentioned ignition apparatus. In addition, the ignition plugs shown in FIGS. 5 and 6 have a structure in which the four-stage multipoint ignition according to the second embodiment of the above mentioned ignition apparatus is possible.

[First Embodiment of Internal-Combustion Engine]

Figure 7:
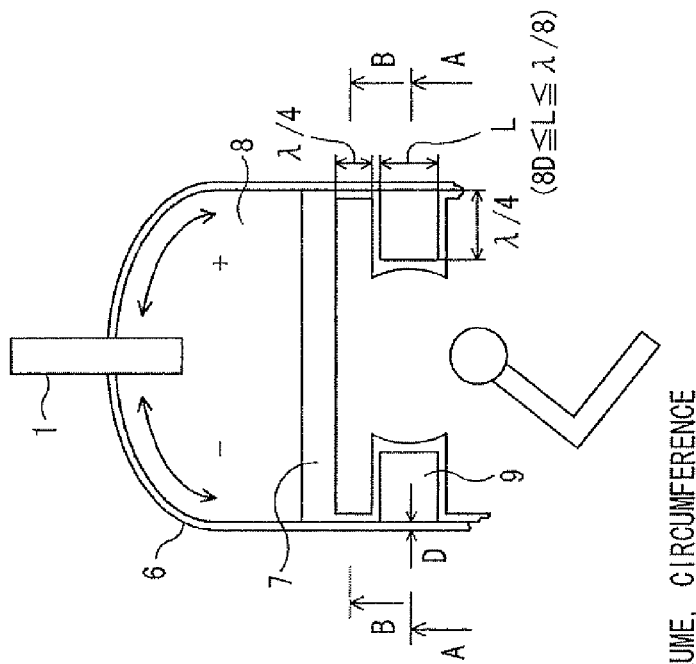
FIG. 7 are a side view and top plan views showing a configuration of a main part of an internal-combustion engine according to a first embodiment of the present invention.

As shown in FIG. 7, an internal-combustion engine according to the present invention is constituted by a cylinder 6 and a piston 7. The internal-combustion engine includes a combustion/reaction chamber 8 provided with mixture of fuel and air and the combustion/reaction of the mixture is carried out. In addition, the internal-combustion engine includes the microwave radiation antenna 1 serving as the ignition apparatus according to the above-mentioned embodiment. In the internal-combustion engine, concave portions 9 for preventing leakage of the microwave are formed on the outer peripheral surface of piston 7 being in sliding contact with the inner wall of the cylinder 6.

The concave portions 9 are intermissive annular grooves surrounding the outer peripheral surface of the columnar piston 7. When the interval between the inner wall of the cylinder 6 and the piston is denoted by D, the wavelength of the microwave is denoted by $\lambda$, the widths (groove widths) L of the concave portions 9 are preferable to be in the range from no fewer than 8 D to nor more than $\lambda/8$. In addition, the depths (groove depths) of the concave portions 9 are set to be $\lambda/4$.

As shown in FIG. 7A, the concave portions 9 cover about 80% of the whole circumference (360 degree) of the outer peripheral surface of the piston 7, thereby preventing the microwave from leaking from the cylinder 6 in the case where the wavelength of the microwave is not disturbed. Further, as shown in FIG. 7B, the concave portions 9 allow the microwave to pass when the wavelength of the microwave is disturbed, and thus the microwave at a specific frequency is selectively trapped, thereby stabilizing the inside of the chamber.

[Second Embodiment of Internal-Combustion Engine]

Figure 8:
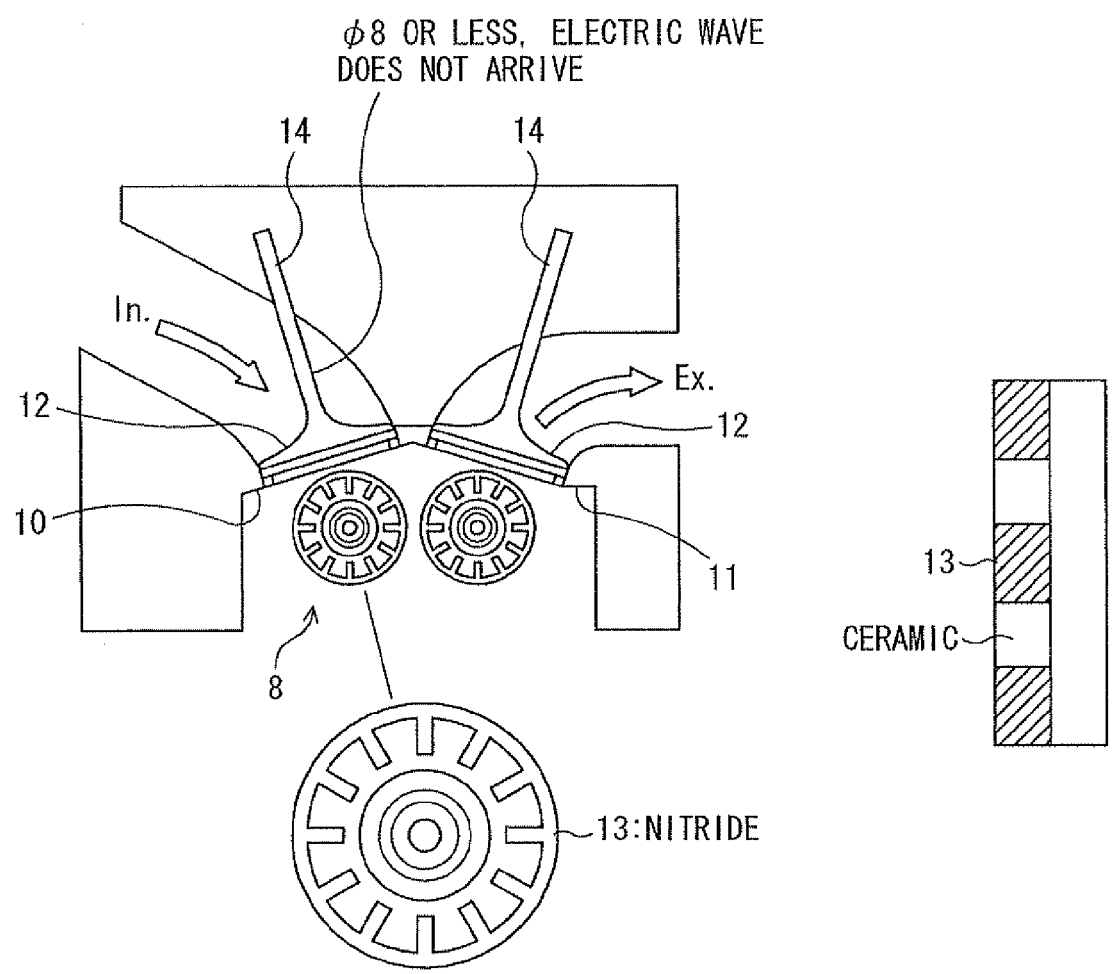
FIG. 8 are sectional views showing a configuration of a main part of an internal-combustion engine according to a second embodiment of the present invention.

As shown in FIG. 8, the internal-combustion engine according to the present invention includes the cylinder and the piston. The internal-combustion engine includes a combustion/reaction chamber 8 provided with mixture of fuel and air and the combustion/reaction of the mixture is carried out, and valves 12 for opening and closing an inlet port 10 and an outlet port 11 provided to the combustion/reaction chamber 8. In addition, the internal-combustion engine includes the microwave radiation means serving as the ignition apparatus according to the above-mentioned embodiment. As described above, the microwave radiation means radiates the microwave into the combustion/reaction chamber 8, thereby at least increasing the temperature of the mixture in the combustion/reaction chamber 8.

Then, in the internal-combustion engine, periodic architectures 13 (for example, a rim bone, a vane strap, and a corrugate) are formed on the surfaces of the valves 12 facing combustion/reaction chamber 8. The periodic architectures 13 resonate with the microwave and focus the microwave for one or more bottom surfaces of the valves 12, that is, for engine combustion chamber side. The periodic architectures 13 are protrusions made in the same shape as the resonator in the magnetron by nitride and the like. In addition, concave portions between the protrusions constituting the periodic architectures 13 are filled with an insulating material such as ceramic, and the surfaces of the valves 12 facing the combustion/reaction chamber 8 are flatly shaped.

In the internal-combustion engine, the microwave is transmitted from the magnetron to the surfaces of the valves 12 facing the combustion/reaction chamber 8 via shafts 14 of the valves 12. Then, the microwave resonates in the periodic architectures 13 of the valves 12, thereby being converted into currents. Accordingly, when the microwave is transmitted to the periodic architectures 13 of the valves 12, sparks occur in the periodic architectures 13. That is, in the internal-combustion engine, ignition of the mixture by sparks can be performed without using spark plugs. In addition, it is preferable that the diameter of the shafts 14 of the valves 12 is 8 mm or less in order to prevent the leakage of the microwave.

In the internal-combustion engine, since the conventional spark plug is not necessary to be provided, there becomes more room. Thus, increase in size of the inlet port 10 and the outlet port 11 can be achieved, thereby improving the efficiency of the combustion/reaction. In addition, in the internal-combustion engine, the multipoint ignition can be performed on the substantially entire surface of each valve 12 facing the combustion/reaction chamber 8, thereby realizing stable combustion/reaction.

In addition, in the internal-combustion engine, not all of energy of the microwave is spent for spark. It is possible to adjust the ratio between the energy spent for spark of the microwave and the energy serving as the microwave radiated into the combustion/reaction chamber 8 by optimizing the output, the pulse width, and the like of the microwave. Therefore, it is possible to configure the ignition apparatus as described above.

Figure 9:
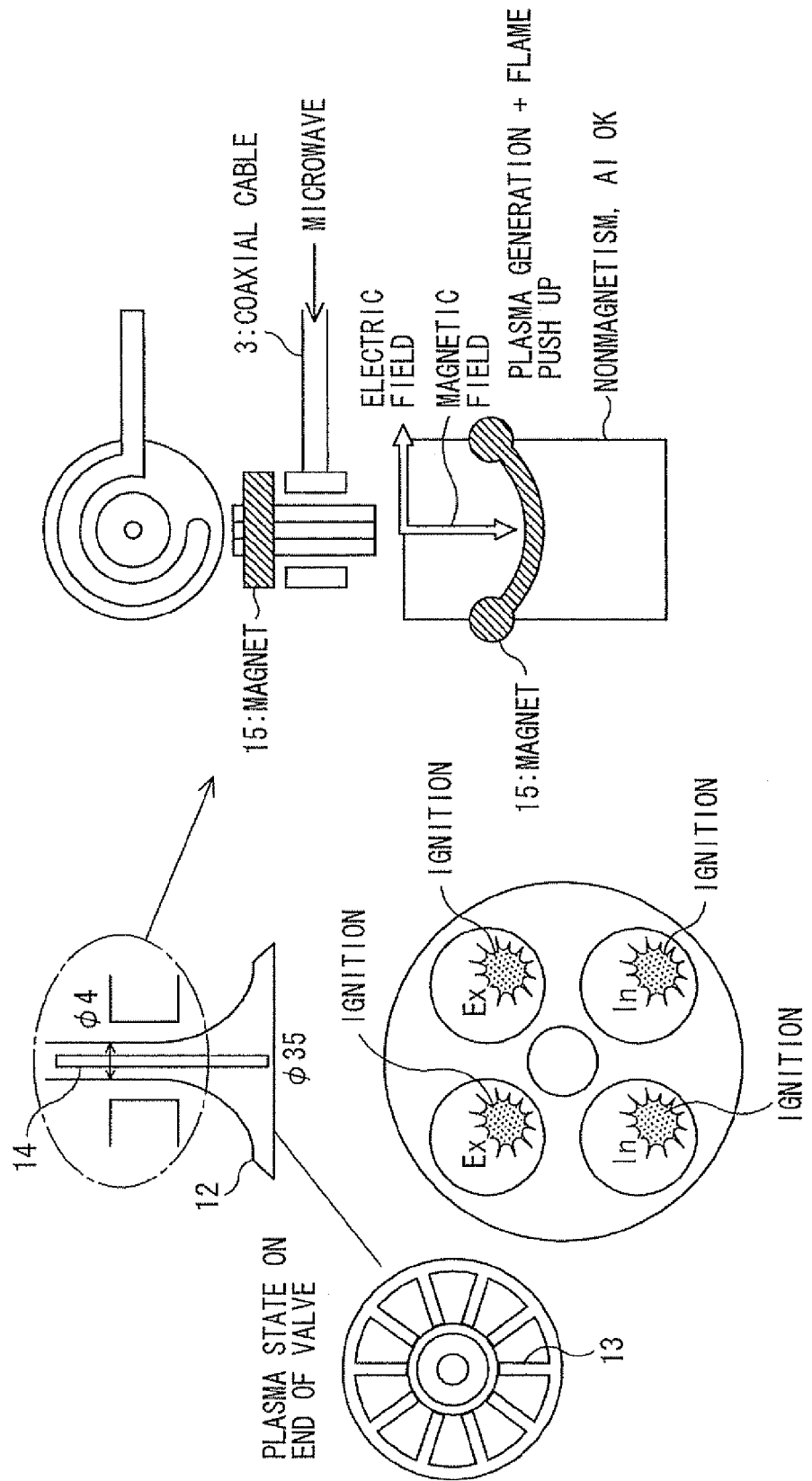
FIG. 9 are side views showing another example of a configuration of an internal-combustion engine according to the present invention.

Further, in the internal-combustion engine, as shown in FIG. 9, a magnetic field and an electric field are generated by providing a magnetic 15 in the proximity of the shaft 14 of the valve 12 to which the microwave is transmitted. Therefore, it is possible to promote the combustion/reaction by plasma generation and promoting the flame propagation.

Figure 10:
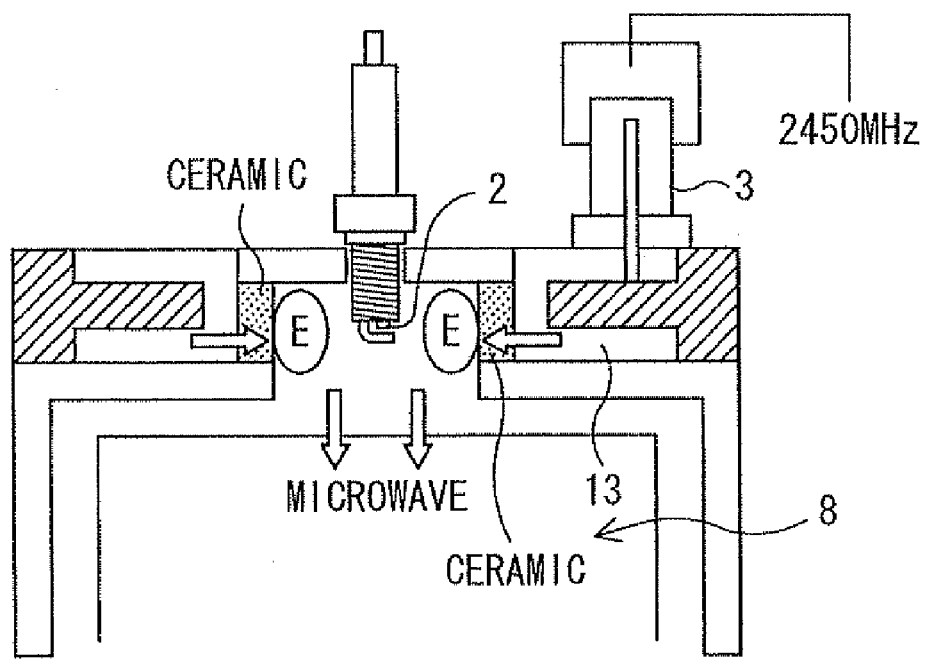
FIG. 10 are sectional views showing another example of a configuration of an internal-combustion engine according to the present invention.
Figure 10:
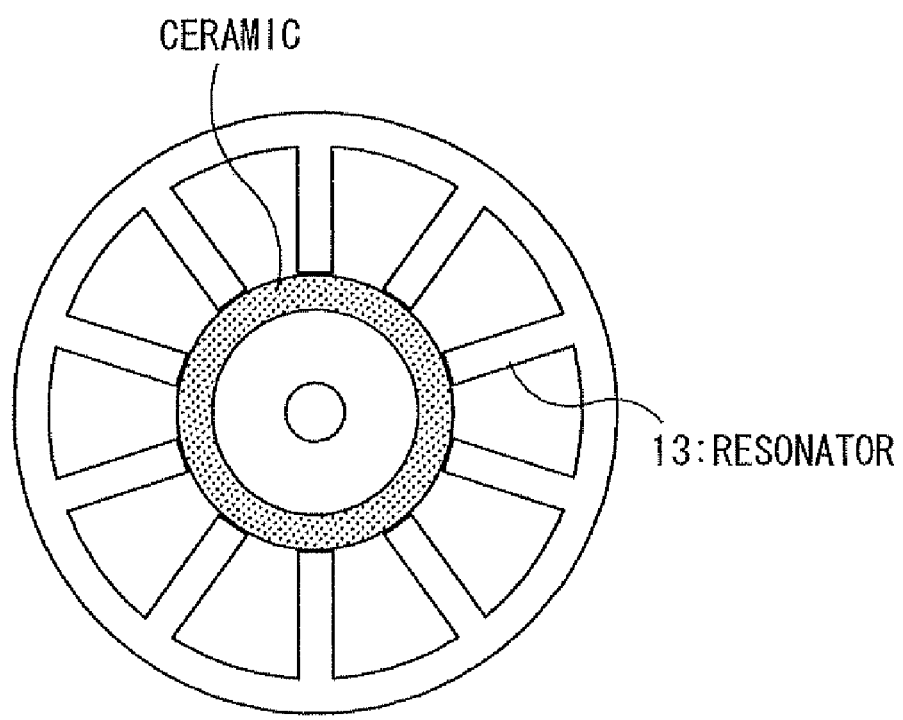

Furthermore, in the internal-combustion engine, as shown in FIG. 10, it is preferable that the periodic architectures 13 (a protrusion of nitride and the like having the same shape as the resonator in the magnetron) resonating with the microwave are provided on the inner wall of the combustion/reaction chamber 8 and the microwave is generated in the periodic architectures 13 by supplying current to the periodic architectures 13.

[First Embodiment of Plasma Equipment]

Figure 11:
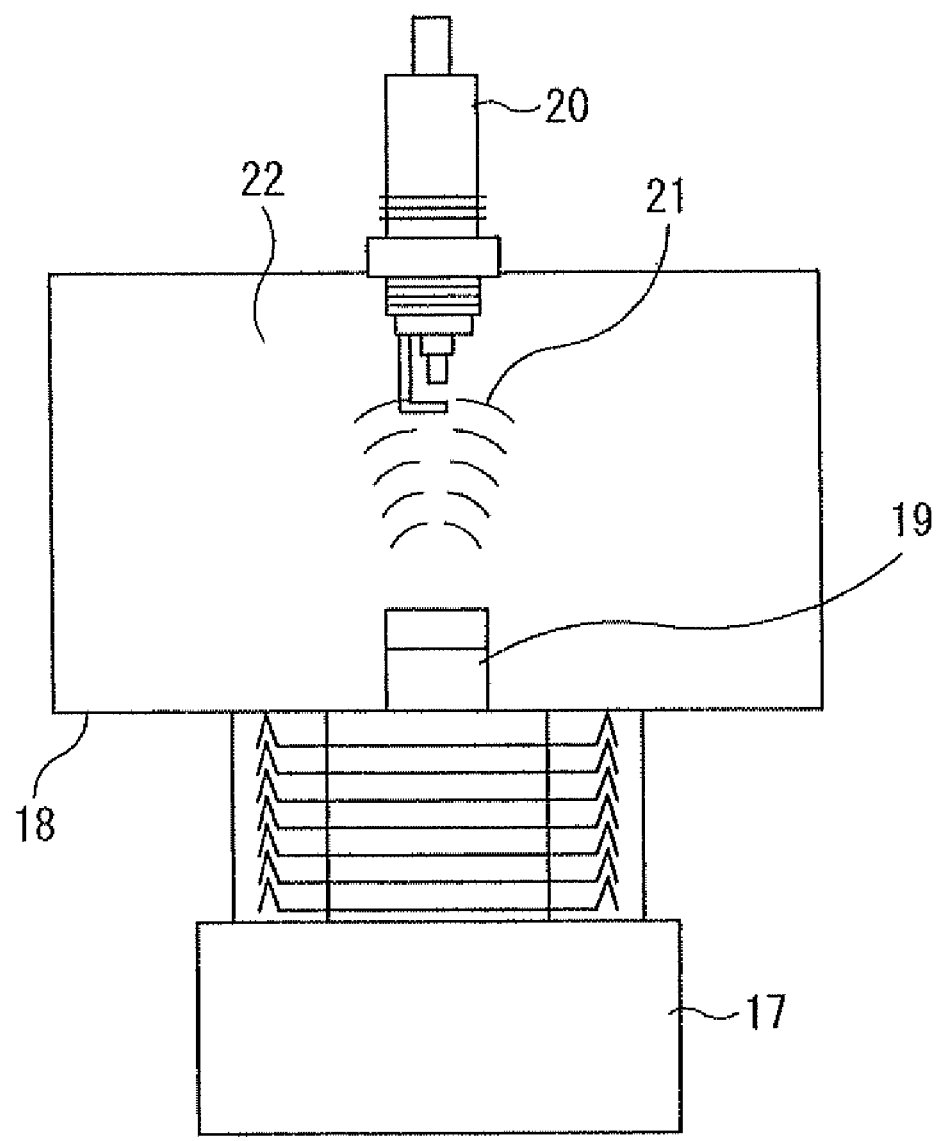
FIG. 11 is a side view showing a configuration of a main part of a plasma equipment according to a first embodiment of the present invention.

As shown in FIG. 11, a plasma equipment according to the present invention includes a microwave oscillator 17, a microwave resonant cavity (cavity) 18 resonating at a predetermined microwave band, microwave radiation means (microwave radiation antenna) 19 for radiating the microwave into the cavity, and plasma ignition means 20 for performing partial electrical discharge to the gas in the cavity to induce plasma in the gas. The microwave radiation antenna 19 forms a strong electric field of the microwave in a plasma generation field 21 by using the plasma ignition means 20.

Thermal nonequilibrium plasma of a high pressure field (atmospheric pressure, or 0.2 MPa or more) is generated in a fluid 22 in the microwave resonant cavity (cavity) to oxidize, react chemically and detoxify hazardous effluents, chemical substances, suspended particulate matter, soot and the like by using products materials of plasma (OH radicals and ozone ($O_3$)). An exceptional merit of the atmospheric thermal nonequilibrium plasma is that the response speed and the material conversion ratio can be controlled substantially independently of temperature and pressure since the restriction of thermochemical equilibrium is avoided. Thus, there is high degree of freedom to design a reactor reacted to the generated plasma. Thus, the reactor can be configured to be light, compact and highly-responsive. The atmospheric thermal nonequilibrium plasma may be used, for example, for direct synthesis of methanol from methane, steam reforming of natural gas, acetylene composition, natural gas liquefaction and the like.

At this time, the pressure of the generated plasma is set to the line pressure of a process fluid of the detoxified hazardous effluents, chemical substances, suspended particulate matter, soot, and the like. In addition, processed quantity is determined by flow rate of a line.

Incidentally, the inventor has carried out various fundamental researches in order to generate the plasma of a high pressure field. Based on the research outcome, it turned that maintenance of stable plasma is possible by igniting a plasma material in some way and supplying energy thereto. For this reason, the plasma ignition means 4 ignites thermal nonequilibrium plasma by using any one of barrier discharge which inserts an insulating material such as a dielectric body between electrodes, corona discharge which forms a non-uniform electric field, and a pulse discharge which applies less than 1 µs of short pulse voltage. For example, the plasma is partially ignited by using electrical discharge of a spark plug for a gasoline vehicle or a glow plug. In order to grow the generated plasma, a strong electric field is formed in the plasma generation field 21 in the proximity of an electrical discharge position of the spark plug or the glow plug by using the microwave transmitted from a microwave transmitter 1. Accordingly, the energy of the microwave is absorbed into the thermal nonequilibrium plasma, thereby the plasma grows (volumetric ignition). In such a process, OH radicals which allow chemical active reaction to occur and $O_3$ having strong oxidizability increase in great numbers by hundreds of times of orders. The reaction is promoted by adding water which is the source of OH radicals and $O_3$. In addition, in order to promote the reaction, it is effective to apply 1 GHz or more of the microwave in which water molecules resonate thereto. As a magnetron for generating the microwave, it is desirable to use the magnetron which has been already manufactured for home electric appliances (for example, a magnetron for a microwave oven having the oscillating frequency of 2.45 GHz) in large quantities all over the world, in view of an apparatus that is easy and inexpensive to manufacture.

In addition, depending on processed objects such as hazardous substance and the like, the microwave radiation means is not limited to the magnetron having an oscillation frequency of 2.45 GHz, but may use a magnetron oscillating at resonance frequency of the hydrocarbon molecule, the carbon molecule, the hydrogen molecule, and the like in fuel. In this case, it is not necessary to introduce water into the combustion field.

[Second Embodiment of Plasma Equipment]

As shown in FIG. 12, the plasma equipment according to the present invention includes the microwave oscillator 17, the microwave resonant cavity (cavity) 18 resonating at a predetermined microwave band, the microwave radiation means 19 (the microwave radiation antenna) for radiating the microwave to the plasma generation field 21 in the cavity, the plasma ignition means 20 for performing partial electrical discharge to gas 22 in the cavity to induce plasma in the gas, a measurement unit 23 for measuring the generation amount or emission intensity of OH radicals and $O_3$ generated by the plasma generation and a control means 24 for controlling input energy/pattern of the microwave radiation means and the plasma ignition means. Arrows in FIG. 12 indicate a flowing direction of a fluid 25 that is processed or burned by the plasma.

As described in the first embodiment, an OH sensor and an $O_3$ sensor of the measurement unit 23 provided on the downstream side performs real-time detection of the generation amount or emission intensity of OH radicals and $O_3$ of the fluid which is detoxified or oxidized by the plasma generation and chemically reacted by OH radicals. Based on the calculated detection result, the microwave radiation means 19 and the plasma ignition means 20 are controlled to the predetermined values under a certain control range, thereby controlling the process amount of the hazardous substance and the like flowing through the plasma equipment.

[Third Embodiment of Plasma Equipment]

Figure 13:
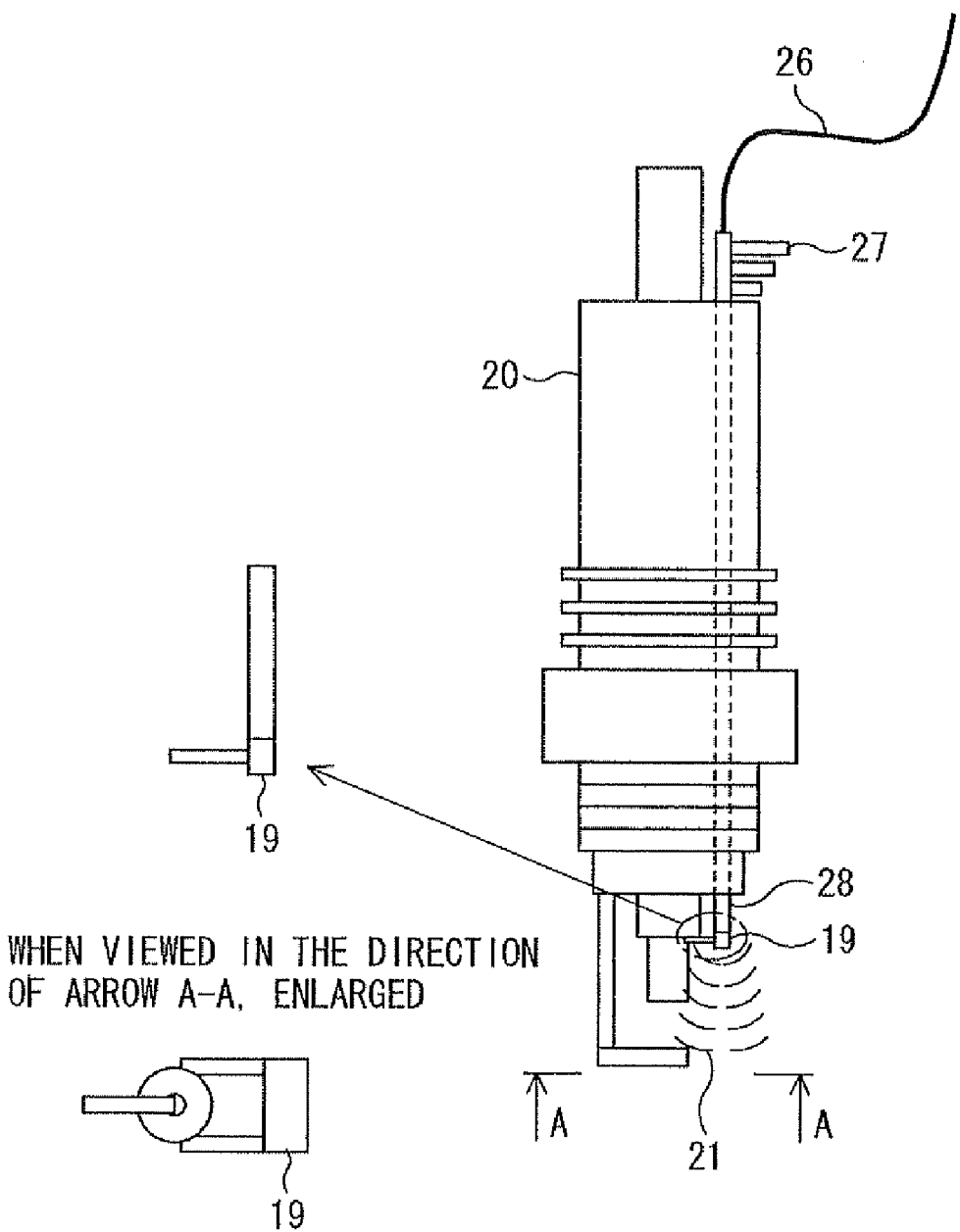
FIG. 13 is a side view showing a configuration of a main part of a plasma equipment according to a third embodiment of the present invention.

As shown in FIG. 13, the plasma equipment according to the present invention makes smaller and less expensive microwave radiation means 19 according to the first embodiment or the second embodiment of the present invention. This is realized by fitting the antenna 19 to the conventional spark plugs or the glow plugs. In this case, an end of the antenna 19 is branched so as to surround the ignition/discharge unit, thereby forming a strong electrical field.

[Fourth Embodiment of Plasma Equipment]

Figure 14:
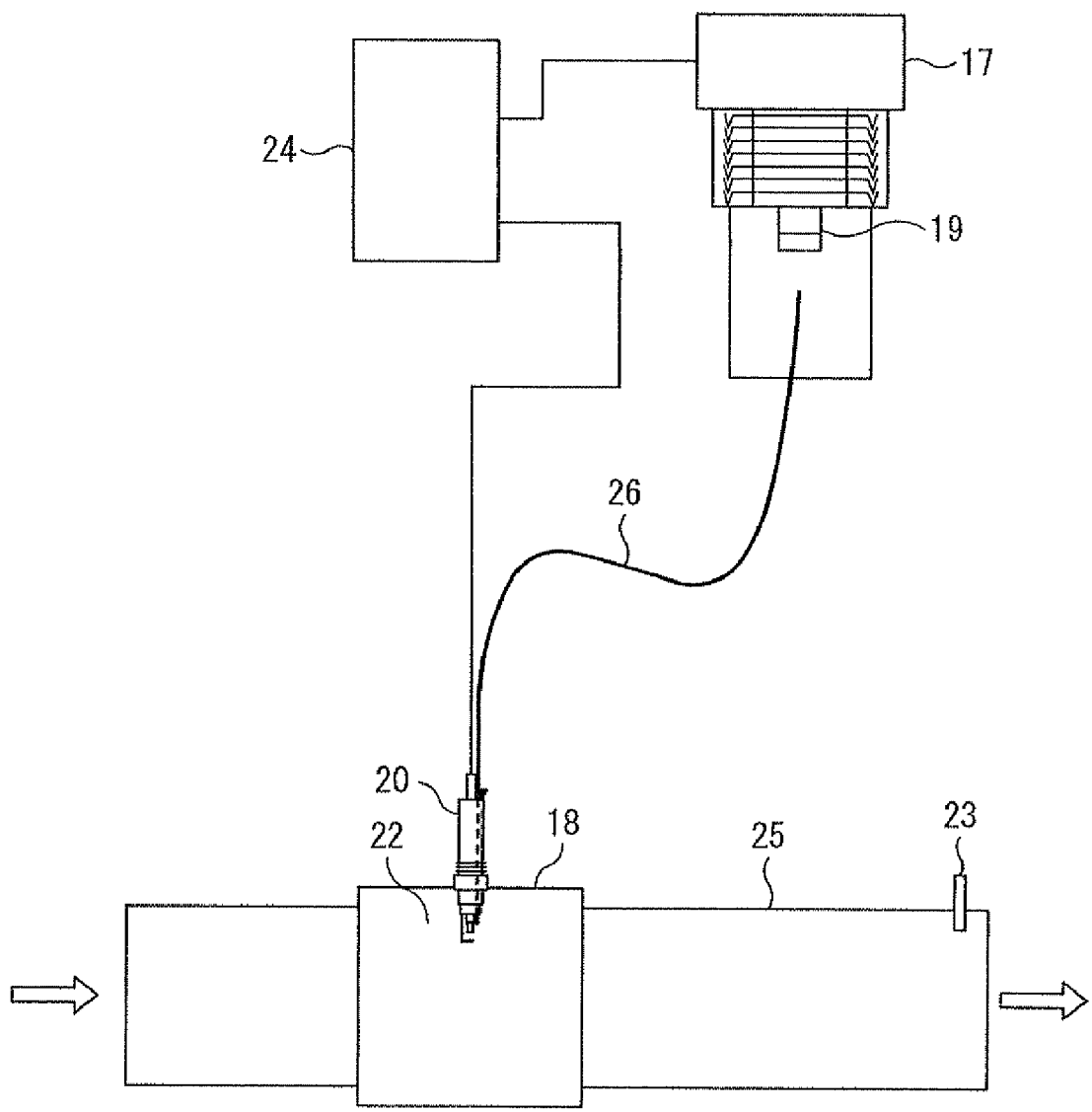
FIG. 14 is a side view showing a configuration of a main part of a plasma equipment according to a fourth embodiment of the present invention. In addition.

As shown in FIG. 14, the plasma equipment according to the present invention includes a coaxial cable 26 for transmitting the microwave, a directional coupler 27 for branching, isolating, and coupling the microwave, and a regulator (stub) 28 for regulating impedance of entire transmission systems according to the first to third embodiments of the present invention. For example, when the present invention is applied to a vehicle engine, the microwave oscillator 17 is not installed in an engine exposed to intense vibration but at a position where vibration and temperature do not vary, so that durability and reliability of the microwave oscillator 17 are improved. In addition, by providing the directional coupler, it is possible to realize an apparatus branching the energy from the microwave oscillator to multipoint in a combustion chamber or online reactor (a position at which hazardous substance and the like are detoxified by plasma) to perform uniform process.

[Fifth Embodiment of Plasma Equipment]

As shown in FIG. 13, the plasma equipment according to the present invention includes a coaxial cable 26 for transmitting the microwave, a directional coupler 27 for branching, isolating, and coupling the microwave, and a regulator (stub) 28 for regulating impedance of entire transmission systems according to the first to third embodiments of the present invention. For example, when the present invention is applied to a vehicle engine, the microwave oscillator 17 is not installed in an engine exposed to intense vibration but at a position where vibration and temperature do not vary, so that durability and reliability of the microwave oscillator 17 are improved. In addition, by providing the directional coupler, it is possible to realize an apparatus branching the energy from the microwave oscillator to multipoint in a combustion chamber or online reactor (a position at which hazardous substance and the like are detoxified by plasma) to perform uniform process.

[First Embodiment of Exhaust Gas Degradation Apparatus]

A basic configuration of an exhaust gas degradation apparatus according to the present invention is the same as that of the plasma equipment in FIG. 12 or 14. As shown in FIG. 12 or 14, the exhaust gas degradation apparatus includes the microwave oscillator 17, the microwave resonant cavity (cavity) 18 resonating at a predetermined microwave band, the microwave radiation means (microwave radiation antenna) 19 for radiating the microwave to the plasma generation field in the cavity, the plasma ignition means 20 for performing partial electrical discharge to the gas 22 in the cavity to induce plasma in the gas, the measurement unit 23 for measuring the generation amount or emission intensity of OH radicals and $O_3$ generated by plasma generation, and the control means 24 for controlling an input energy/pattern of the microwave radiation means and the plasma ignition means. Arrows in a drawing indicate a flowing direction of an exhaust gas fluid 25 that is processed or burned by the plasma.

As described in the above-mentioned first embodiment, exhaust gases such as unburned gas, soot, $NO_x$ and the like in the combustion/reaction chamber are detoxified into stable and nonhazardous oxide and carbon such as $NO_2$ and $CO_2$ by breaking and oxidizing carbon-carbon bond and carbon-hydrogen bond by strong oxidizability of ozone and OH radicals accompanied with plasma generation and chemically reacting by OH radicals. The OH sensor and $O_3$ sensor of the measurement unit 6 provided on the downstream side measures in real time the generation amount or emission intensity of OH radicals and $O_3$. Based on the calculated measurement result, the microwave radiation means 19 and the plasma ignition means 20 are controlled to the predetermined values under a certain control range, thereby it is possible to control the process amount of the hazardous substance and the like flowing through the plasma equipment.

[Example of Use of Ozone Generating/Sterilizing/Disinfecting Apparatus and Odor Eliminating Apparatus]

For example, when the present invention is applied to a jet engine for an aircraft, the present apparatus is installed in the proximity of a jet engine exhaust cone, and thus high pressure steam containing moisture can be converted into a great amount of OH radicals and $O_3$ by using the thermal nonequilibrium plasma generated in the present apparatus. The atmosphere has been polluted by exhaust gases of aircraft, but it is possible to degrade the exhaust gas into nonhazardous gas by a great amount of OH radicals and $O_3$ which have strong oxidizability. Further, it is possible to generate a great amount of $O_3$ so as to restore the ozone layer in the stratosphere which has been damaged by CFC and the like.

In addition, it is possible to promote combustion of compressed mixed fuel using strong radical reaction by installing the present apparatus at a combustion chamber located at a rear stage of a jet engine high-pressure compressor. Accordingly, it is possible to contribute to environmental conservation by discharging clean exhaust gas instead of exhaust gas polluting the atmosphere. The OH sensor and $O_3$ sensor of the measurement unit 6 provided on the downstream side measures in real time the generation amount or emission intensity of OH radicals and $O_3$. Based on the calculated measurement result, the microwave radiation means and the plasma ignition means are controlled to the predetermined values under a certain control range, thereby it is possible to control the production amount of the hazardous substance and the like by controlling combustion in the combustion chamber.

[Example of Use of Internal-Combustion Engine and Plasma Equipment According to the Present Invention]

Even when biogas, very lean methane gas, very low calorie gas and the like are used as fuel of the internal-combustion engine and the plasma equipment according to the present invention, chemical reaction can be promoted by using strong oxidizability of OH radicals and the $O_3$ generated by the plasma generation. Therefore, it is now possible to burn these gases in a normal gas engine without help of additional gases. Further, it is possible to improve output, electric generation efficiency and the like.

[Example of Use of Plasma equipment According to the Present Invention]

A great amount of spectral light can be generated from $N_2$ contained in the air by using the plasma equipment according to the present invention in the atmospheric pressure air. When the spectrum is focused and then derived via fiber and the like, it is possible to provide an inexpensive and compact $N_2$ spectral source and a pulse source in place of an expensive, conventional laser source.

[Example of Use of Ozone Generating/Sterilizing/Disinfecting Apparatus and Odor Eliminating Apparatus According to the Present Invention]

When the apparatus according to the present invention is installed at a corner in a building located in a construction site and then operated in a state where the building is closed, substances causing the sick house syndrome are removed, various odors of paints, adhesive pastes, antiseptic agents and the like are deodorized, and bacteria, viruses and allergic substances are sterilized and disinfected. In this case, it is possible to discharge post-processed detoxified air by installing the apparatus according to the present invention at a rear stage of a simple air exhauster located in a construction site. Alternatively, by fitting the present apparatus into a cleaner which is a general home electric appliance, it is possible to degrade hazardous substances on a surface of cleaned objects by OH radicals and $O_3$ generated in the present apparatus during cleaning. Although an architectural structure (communal facility, building, gym, auditorium, shopping mall, and so forth) is described as an object, it is possible to get the most out of the same effect by applying the present invention to sterilization, deodorization, and disinfection of an object which has an arbitrary closed space such as a vehicle, a train, a cargo, an airplane, a ship, a submarine, or a tank. Further, when $H_2O$ (moisture) is added thereto at the time of generating plasma, more OH radicals and the like are generated, thereby improving the effect.

In addition, the present apparatus may be applied to air cleaning and carbon monoxide poisoning prevention in case of fire in facilities such as a communal facility, a building, a gym, an auditorium, a shopping mall and a tunnel, thereby contributing to a lifesaving such as detoxification in which the carbon monoxide is changed into the carbon dioxide and smoke removal.

[Industrial Applicability]

The present invention may be used as an ignition apparatus used in a heat engine such as a reciprocating engine, a rotary engine, a jet engine and a gas turbine, or a plasma equipment, for example.

The present invention may be used for an internal-combustion engine to which the ignition apparatus according to the present invention is suitably applied.

The present invention may be used for an ignition plug that is suitably applied to the ignition apparatus according to the present invention.

The present invention may be used for a plasma equipment used in an environmental (an in-plant and an end-of-pipe) countermeasure field such as decrease and reduction of hazardous effluents ($CO_2$, $NO_x$ and unburnt hydrocarbon), volatile organic compounds (VOC), suspended particulate matters (PM), soot and the like or process and reuse of tar, sludge, and drainage, and a medical/hygiene field such as sterilization, pasteurization and cleaning technology.

The invention may be used for an exhaust gas degradation apparatus to which the plasma equipment according to the present invention is suitably applied.

The present invention may be used for an ozone generating/sterilizing/disinfecting apparatus and an odor eliminating apparatus to which the plasma equipment according to the present invention is suitably applied.

The invention claimed is:

1. An internal-combustion engine comprising:
   a combustion/reaction chamber including a cylinder and a piston where mixture of reactive gas and oxidation gas is provided and combustion/reaction or plasma reaction of the mixture are carried out; and
   a microwave radiator radiating microwave into the combustion/reaction chamber for making plasma discharge in the combustion/reaction chamber,
   wherein concave portions for preventing leakage of the microwave are formed on an outer peripheral surface of the piston coming in contact with an inner wall of the cylinder, and
   wherein the piston is columnar and the concave portions are intermissive annular grooves surrounding an outer peripheral surface of the piston.

2. The internal-combustion engine according to claim 1, wherein a groove widths of the concave portions are no more than one-eighth of wavelength of the microwave.

3. The internal-combustion engine according to claim 2, wherein the groove widths of the concave portions are no less than eight times of an interval between the inner wall of the cylinder and the piston.

4. An internal-combustion engine comprising:
   a combustion/reaction chamber including a cylinder and a piston where mixture of reactive gas and oxidation gas is provided and combustion/reaction or plasma reaction of the mixture are carried out;
   an auto-igniter automatically igniting the mixture by compressing the mixture of the reactive gas and the oxidation gas to increase temperature;
   a microwave radiator radiating the microwave into the combustion/reaction chamber; and
   a controller controlling the auto-igniter and the microwave radiator,
   wherein the microwave radiator and the auto-igniter are controlled by the controller so as to repeat a cycle that is a process by which the microwave radiator radiates the microwave into the combustion/reaction chamber so that a great amount of hydroxyl radical and ozone are generated from moisture of the mixture in the combustion/reaction chamber and then oxidizes and reacts chemically; and the auto-igniter ignites the mixture, so that the combustion of the mixture in the combustion/reaction chamber is promoted by the great amount of hydroxyl radical and ozone.

\* \* \* \* \*